US012378206B2

(12) United States Patent
Bollbuck et al.

(10) Patent No.: US 12,378,206 B2
(45) Date of Patent: Aug. 5, 2025

(54) HETEROARYL BUTANOIC ACID DERIVATIVES

(71) Applicant: NOVARTIS AG, Basel (CH)

(72) Inventors: Birgit Bollbuck, Munich (DE); Christian Markert, Riehen (CH); Wolfgang Miltz, Allschwil (CH); Till Roehn, Zurich (CH)

(73) Assignee: Novartis AG, Basel (CH)

( * ) Notice: Subject to any disclaimer, the term of this patent is extended or adjusted under 35 U.S.C. 154(b) by 454 days.

(21) Appl. No.: 17/820,348

(22) Filed: Aug. 17, 2022

(65) Prior Publication Data

US 2022/0411385 A1 Dec. 29, 2022

Related U.S. Application Data

(60) Continuation of application No. 15/895,224, filed on Feb. 13, 2018, now Pat. No. 11,453,651, which is a division of application No. 15/104,729, filed as application No. PCT/IB2014/067086 on Dec. 18, 2014, now Pat. No. 9,981,926.

(30) Foreign Application Priority Data

Dec. 20, 2013 (EP) .................................... 13199138
Aug. 15, 2014 (EP) .................................... 14181155

(51) Int. Cl.
| C07D 401/12 | (2006.01) |
| A61K 31/41 | (2006.01) |
| A61K 31/415 | (2006.01) |
| A61K 31/422 | (2006.01) |
| A61K 31/4245 | (2006.01) |
| A61K 31/428 | (2006.01) |
| A61K 31/4439 | (2006.01) |
| A61K 45/06 | (2006.01) |
| C07D 231/12 | (2006.01) |
| C07D 257/04 | (2006.01) |
| C07D 271/10 | (2006.01) |
| C07D 413/12 | (2006.01) |
| C07D 417/12 | (2006.01) |

(52) U.S. Cl.
CPC ............ *C07D 257/04* (2013.01); *A61K 31/41* (2013.01); *A61K 31/415* (2013.01); *A61K 31/422* (2013.01); *A61K 31/4245* (2013.01); *A61K 31/428* (2013.01); *A61K 31/4439* (2013.01); *A61K 45/06* (2013.01); *C07D 231/12* (2013.01); *C07D 271/10* (2013.01); *C07D 401/12* (2013.01); *C07D 413/12* (2013.01); *C07D 417/12* (2013.01)

(58) Field of Classification Search
CPC .............. C07D 401/12; C07D 291/04
See application file for complete search history.

(56) References Cited

U.S. PATENT DOCUMENTS

| 4,851,423 A | 7/1989 | Girijavallabhan et al. |
| 5,272,167 A | 12/1993 | Girijavallabhan et al. |
| 5,459,144 A | 10/1995 | Girijavallabhan et al. |
| 5,750,532 A | 5/1998 | Girijavallabhan et al. |
| 6,037,345 A | 3/2000 | Pamukcu et al. |
| 2002/0107244 A1 | 8/2002 | Howard |
| 2002/0123490 A1 | 9/2002 | Howard |
| 2008/0194630 A1 | 8/2008 | Barchuk et al. |
| 2008/0293720 A1* | 11/2008 | Cleary .................... A61P 35/00 514/342 |
| 2018/0170887 A1 | 6/2018 | Bullock et al. |

FOREIGN PATENT DOCUMENTS

| EP | 0260817 A1 | 3/1988 |
| EP | 0276065 A1 | 7/1988 |
| EP | 0300100 A1 | 1/1989 |
| EP | 0303478 A1 | 2/1989 |
| EP | 0388967 A1 | 9/1990 |
| EP | 0407217 A1 | 1/1991 |
| EP | 0274867 B1 | 4/1994 |
| EP | 0560407 B1 | 5/1996 |
| EP | 1262197 A2 | 12/2002 |
| GB | 2144125 A | 2/1985 |
| WO | 199100858 A1 | 1/1991 |
| WO | 1996036617 A1 | 11/1996 |
| WO | 2000047188 A1 | 8/2000 |
| WO | 2000050577 A1 | 8/2000 |
| WO | 2000057877 A1 | 10/2000 |
| WO | 2001085166 A1 | 11/2001 |
| WO | 2004002409 A2 | 1/2004 |
| WO | 2004035741 A2 | 4/2004 |

(Continued)

OTHER PUBLICATIONS

Jamieson et al. "Positional Scanning for Peptide Secondary Structure by Systematic Solid-Phase Synthesis of Amino Lactam Peptides." J. Am. Chem. Soc. 2009, 131, 7917. (Year: 2009)*
Kachur, et al., "Pharmacological Characterization of SC-57461A (3-[Methyl[3-[4-(phenylmethyl)phenoxy] propyl]amino]propanoic Acid HCl), a Potent and Selective Inhibitor of Leukotriene A4 Hydrolase II: In Vivo Studies", The Journal of Pharmacology and Experimental Therapeutics, 2002, pp. 583-587, vol. 300(2).
Di Gennaro et al., "The Leukotrienes: Immune-Modulating Lipid Mediators of Disease", Advances in Immunology, 2012, pp. 51-92, Chapter 2, vol. 16.
Caliskan, et al., ""Overview of recent drug discovery approaches for new generationleukotriene A4 hydrolase Inhibitors", Expert opinion on drug discovery", 2013, pp. 49-63, 8(1).

(Continued)

Primary Examiner — Amanda L. Aguirre
(74) Attorney, Agent, or Firm — Francine F. Li

(57) ABSTRACT

The present invention describes novel heteroaryl butanoic acid derivatives that are good drug candidates especially with regard to leukotriene A4 hydrolase (LTA4H). The present invention also relates to pharmaceutical compositions comprising said novel heteroaryl butanoic acid derivatives, methods of using said compounds in the treatment of various diseases and disorders, and processes for preparing the said novel compounds.

1 Claim, No Drawings

(56) References Cited

FOREIGN PATENT DOCUMENTS

| WO | 2004099783 A2 | 11/2004 |
|---|---|---|
| WO | 2005027886 A2 | 3/2005 |
| WO | 2005107725 A1 | 11/2005 |
| WO | 2006008142 A1 | 1/2006 |
| WO | 2006105439 A2 | 10/2006 |
| WO | 2007020013 A2 | 2/2007 |
| WO | 2008019284 A1 | 2/2008 |
| WO | 2008019306 A2 | 2/2008 |
| WO | 2008079291 | 7/2008 |
| WO | 2008098977 A1 | 8/2008 |
| WO | 2008117970 A1 | 10/2008 |
| WO | 2012018980 A2 | 2/2012 |
| WO | 2013142369 A1 | 9/2013 |
| WO | 2014014874 A1 | 1/2014 |
| WO | 2014165090 A1 | 10/2014 |
| WO | 2015009609 A1 | 1/2015 |

OTHER PUBLICATIONS

Thangapandian, et al., "Molecular docking and pharmacophore filtering in the discovery of dual-inhibitors for human leukotriene A4 hydrolase and leukotriene C4 synthase", J Chem Inf Model. 2011, pp. 33-44, 51(1).

Hamze, et al., "Synthesis of (R) and (S) enantiomers of Fmoc-protected 1,2,4-oxadiazole-containing β3-amino acids from Fmoc-(R)-β-HAsp(OtBu)-OH", Tetrahedron Letters, 2003, pp. 6079-6082, vol. 44(32).

Hughes, et al., "Effective Methods for the Synthesis of N-Methyl b-Amino Acids from AllTwenty Common a-Amino Acids Using 1,3-Oxazolidin-5-ones and 1,3-Oxazinan-6-ones", Helvetica Chimica Acta, 2006, pp. 2611-2637, vol. 89 (11).

Hughes et al., "Synthesis of New . . . ", Australian Journal of Chemistry, 2005, vol. 58(11), pp. 7787-784.

\* cited by examiner

HETEROARYL BUTANOIC ACID DERIVATIVES

The present invention describes novel heteroaryl butanoic acid derivatives that are good drug candidates especially with regard to leukotriene A4 hydrolase (LTA4H). The present invention also relates to pharmaceutical compositions comprising said novel heteroaryl butanoic acid derivatives, methods of using said compounds in the treatment of various diseases and disorders, and processes for preparing the said novel compounds.

FIELD OF THE INVENTION

The present invention relates to compounds of formula (I) or pharmaceutically acceptable salts thereof, and to their use in inhibiting LTA4H. Hence the compounds of the invention may be useful in the treatment of diseases and/or disorders related to LTA4H. Such diseases and/or disorders typically include acute and chronic inflammation and autoinflammatory disorders such as inflammatory bowel disease, neutrophilic dermatoses, allergy, fibrotic diseases, vasculitides, arthritides, cardiovascular diseases including atherosclerosis, myocardial infarction and stroke, and cancer. The present invention further relates to pharmaceutical compositions comprising said novel heteroaryl butanoic acid derivatives of formula (I), methods of using said compounds in the treatment of various diseases and disorders, and processes for preparing the said novel compounds.

BACKGROUND OF THE INVENTION

Leukotriene A4 hydrolase (LTA4H) catalyzes the hydrolysis of LTA4 to produce LTB4. LTB4 stimulates an array of pro-inflammatory responses for example where leukocyte chemotaxis or cytokine release may be implicated. Inhibition of LTA4H furthermore elevates biosynthesis of anti-inflammatory, pro-resolving lipoxin A4 which can promote resolution of chronic inflammation. LTA4H inhibition may therefore be of benefit in diseases where chronic, non-resolving inflammation might be a critical component of the pathology and appear to include a broad range of autoinflammatory and autoimmune diseases (see for example Anne M Fourie, Current Opinion in Invest. Drugs 2009, 10, 1173-1182).

SUMMARY OF THE INVENTION

The present invention relates to novel compounds of formula (I) and/or pharmaceutically acceptable salts thereof, and to their use in inhibiting LTA4H, and may further include the treatment of diseases and/or disorders such as allergy, pulmonary, fibrotic, inflammatory, cardiovascular diseases including atherosclerosis, myocardial infarction and stroke, and cancer.

More particularly, in embodiment 1 the present invention relates to a compound of formula (I) or a pharmaceutically acceptable salt thereof;

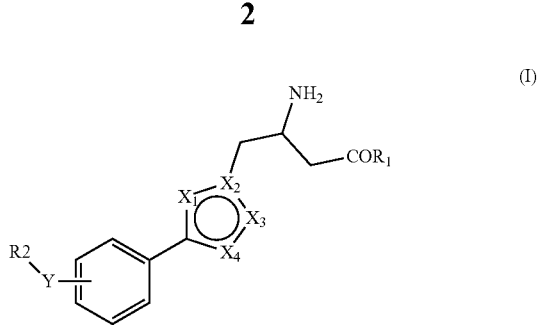

wherein,
R1 is OH or $NH_2$;
Y is O, S or $CH_2$;
X1, X2, X3 and X4 are N; or
X1, X2, X3 and X4 are selected from N, NH, C, CH and O with the proviso that at least two of X1, X2, X3 or X4 are N or NH;
R2 is $C_1$-$C_6$ alkyl optionally substituted by phenyl; $C_3$-$C_6$ cycloalkyl; phenyl optionally being substituted by halogen, cyano, $C_1$-$C_6$ alkyl optionally substituted by halogen, $C_1$-$C_6$ alkoxy, or a 5-6 membered heteroaryl ring containing 1 to 3 heteroatoms selected from N, O and S; or a 5-10 membered mono- or bicyclic heteroaryl containing 1 to 4 heteroatoms selected from N, O and S said heteroaryl being optionally substituted by $C_1$-$C_6$ alkyl optionally substituted by halogen, cyano, or halogen.

The inner circle in the 5 membered ring shown in formula (I) means that the ring is an aromatic ring, and hence the members X1, X2, X3 and/or X4 have to be selected accordingly not to violate aromaticity.

The 3-amino-butanoate side chain shown throughout the invention, e.g. in formula (I), (II), (III), (IV) or (V) typically contains a chiral center (carbon atom carrying the amino group). If not indicated otherwise, a compound of formula (I) encompasses racemic and/or chiral (S)- or (R)-forms.

DETAILED DESCRIPTION OF THE INVENTION

In its broadest embodiment (embodiment 1) the present invention relates to a compound of formula (I) and/or a pharmaceutically acceptable salt thereof as described above in the section Summary of the Invention.

Embodiment 2 of the present invention relates to a compound of formula (I) or a pharmaceutically acceptable salt thereof, wherein R1 is OH or $NH_2$; Y is O; X1, X2, X3 and X4 are N; and
R2 is phenyl optionally being substituted by halogen, cyano, $C_1$-$C_6$ alkyl optionally substituted by halogen, $C_1$-$C_6$ alkoxy, or a 5-6 membered heteroaryl ring containing 1 to 3 heteroatoms selected from N, O and S; or
R2 is a 5-10 membered mono- or bicyclic heteroaryl containing 1 to 4 heteroatoms selected from N, O and S said heteroaryl being optionally substituted by $C_1$-$C_6$ alkyl optionally substituted by halogen, cyano or halogen.

Embodiment 3 of the present invention relates to a compound of formula (I) or a pharmaceutically acceptable salt thereof, wherein R1 is OH or $NH_2$; Y is $CH_2$; X1, X2, X3 and X4 are N; and
R2 is phenyl optionally being substituted by halogen, cyano, $C_1$-$C_6$ alkyl optionally substituted by halogen, C$_1$-C$_6$ alkoxy, or a 5-6 membered heteroaryl ring containing 1 to 3 heteroatoms selected from N, O and S; or R2 is a 5-10 membered mono- or bicyclic heteroaryl containing 1 to 4 heteroatoms selected from N, O and S said heteroaryl being optionally substituted by C$_1$-C$_6$ alkyl optionally substituted by halogen, cyano or halogen.

Embodiment 4 of the present invention relates to a compound of formula (I) or a pharmaceutically acceptable salt thereof; wherein R1 is OH or NH$_2$; Y is O; X1, X2, X3 and X4 are selected from N, NH, C, CH and O with the proviso that at least two of X1, X2, X3 or X4 are N or NH; and R2 is phenyl optionally being substituted by halogen, cyano, C$_1$-C$_6$ alkyl optionally substituted by halogen, C$_1$-C$_6$ alkoxy, or a 5-6 membered heteroaryl ring containing 1 to 3 heteroatoms selected from N, O and S; or R2 is a 5-10 membered mono- or bicyclic heteroaryl containing 1 to 4 heteroatoms selected from N, O and S said heteroaryl being optionally substituted by C$_1$-C$_6$ alkyl optionally substituted by halogen, cyano or halogen.

Embodiment 5 of the present invention relates to a compound of formula (I) or a pharmaceutically acceptable salt thereof; wherein R1 is OH or NH$_2$; Y is CH$_2$; X1, X2, X3 and X4 are selected from N, NH, C, CH and O with the proviso that at least two of X1, X2, X3 or X4 are N or NH; and R2 is phenyl optionally being substituted by halogen, cyano, C$_1$-C$_6$ alkyl optionally substituted by halogen, C$_1$-C$_6$ alkoxy, or a 5-6 membered heteroaryl ring containing 1 to 3 heteroatoms selected from N, O and S; or R2 is a 5-10 membered mono- or bicyclic heteroaryl containing 1 to 4 heteroatoms selected from N, O and S said heteroaryl being optionally substituted by C$_1$-C$_6$ alkyl optionally substituted by halogen, cyano or halogen.

Embodiment 6 relates to any one of the embodiments 1-5 or a pharmaceutically acceptable salt thereof, wherein Y is attached in the para-position of the phenyl moiety.

Embodiment 7 relates to any one of the embodiments 1-5 or a pharmaceutically acceptable salt thereof, wherein Y is attached in the meta-position of the phenyl moiety.

Embodiment 8 of the present invention relates to a compound of formula (I) or a pharmaceutically acceptable salt thereof; wherein R1 is OH or NH$_2$; Y is O; X1, X2, X3 and X4 are N; and R2 is C$_1$-C$_6$ alkyl optionally substituted by phenyl; or C$_3$-C$_6$ cycloalkyl.

Embodiment 9 of the present invention relates to a compound of formula (I) or a pharmaceutically acceptable salt thereof; wherein R1 is OH or NH$_2$; Y is CH$_2$; X1, X2, X3 and X4 are N; and R2 is C$_1$-C$_6$ alkyl optionally substituted by phenyl; or C$_3$-C$_6$ cycloalkyl.

Embodiment 10 of the present invention relates to a compound of formula (I) or a pharmaceutically acceptable salt thereof; wherein R1 is OH or NH$_2$; Y is O; X1, X2, X3 and X4 are selected from N, NH, C, CH and O with the proviso that at least two of X1, X2, X3 or X4 are N or NH; and R2 is C$_1$-C$_6$ alkyl optionally substituted by phenyl; or C$_3$-C$_6$ cycloalkyl.

Embodiment 11 of the present invention relates to a compound of formula (I) or a pharmaceutically acceptable salt thereof; wherein R1 is OH or NH$_2$; Y is CH$_2$; X1, X2, X3 and X4 are selected from N, NH, C, CH and O with the proviso that at least two of X1, X2, X3 or X4 are N or NH; and R2 is C$_1$-C$_6$ alkyl optionally substituted by phenyl; or C$_3$-C$_6$ cycloalkyl.

Embodiment 12 relates to any one of the embodiments 8-11 or a pharmaceutically acceptable salt thereof; wherein Y is attached in the para-position of the phenyl moiety.

Embodiment 13 relates to any one of the embodiments 8-11 or a pharmaceutically acceptable salt thereof; wherein Y is attached in the meta-position of the phenyl moiety.

Embodiment 14 relates to a compound of embodiment 1 which is a compound of formula (II) or a pharmaceutically acceptable salt thereof,

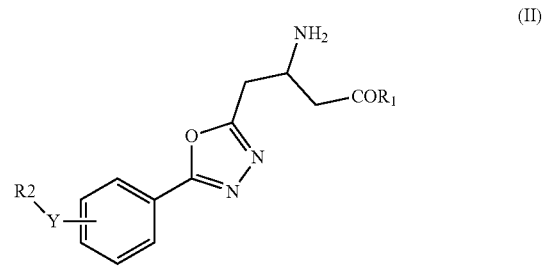

wherein the variables R1, R2 and Y have the meaning as defined in embodiment 1.

Embodiment 15 relates to a compound of embodiment 1 which is a compound of formula (III) or a pharmaceutically acceptable salt thereof,

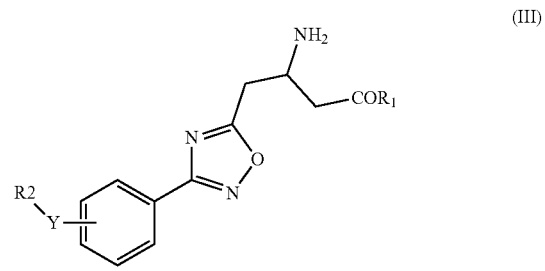

wherein the variables R1, R2 and Y have the meaning as defined in embodiment 1.

Embodiment 16 relates to a compound of embodiment 1 which is a compound of formula (IV) or a pharmaceutically acceptable salt thereof,

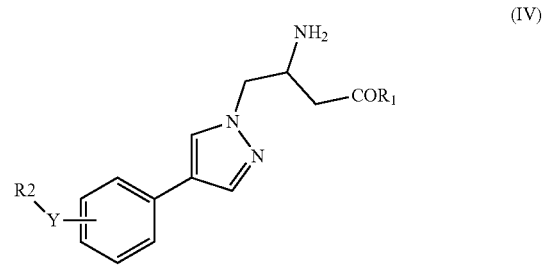

wherein the variables R1, R2 and Y have the meaning as defined in embodiment 1.

Embodiment 17 relates to any one of the embodiments 14-16 or a pharmaceutically acceptable salt thereof, wherein Y is attached in the para-position of the phenyl moiety.

Embodiment 18 relates to any one of the embodiments 14-16 or a pharmaceutically acceptable salt thereof, wherein Y is attached in the meta-position of the phenyl moiety.

Embodiment 19 relates to any one of the embodiments 14-18 or a pharmaceutically acceptable salt thereof, wherein R2 is $C_1$-$C_6$ alkyl optionally substituted by phenyl; or $C_3$-$C_6$ cycloalkyl.

Embodiment 20 relates to any one of the embodiments 14-18 or a pharmaceutically acceptable salt thereof, wherein R2 is phenyl optionally being substituted by halogen, cyano, $C_1$-$C_6$ alkyl optionally substituted by halogen, $C_1$-$C_6$ alkoxy, or a 5-6 membered heteroaryl ring containing 1 to 3 heteroatoms selected from N, O and S; or R2 is a 5-10 membered mono- or bicyclic heteroaryl containing 1 to 4 heteroatoms selected from N, O and S said heteroaryl being optionally substituted by $C_1$-$C_6$ alkyl optionally substituted by halogen, cyano or halogen.

Embodiment 21 relates to any one of the embodiments 14-18 or a pharmaceutically acceptable salt thereof, wherein R2 is a 5-10 membered mono- or bicyclic heteroaryl containing 1 to 4 heteroatoms selected from N, O and S said heteroaryl being optionally substituted by $C_1$-$C_6$ alkyl optionally substituted by halogen, cyano or halogen.

Embodiment 22 relates to any one of the embodiments 1-21 or a pharmaceutically acceptable salt thereof, wherein R1 is OH.

Embodiment 23 relates to a compound of formula (I) in accordance to the embodiments 1-13 or a pharmaceutically acceptable salt thereof; wherein the amino group has the (R)-configuration.

Embodiment 24 relates to a compound of formula (I) in accordance to the embodiments 1-13 or a pharmaceutically acceptable salt thereof; wherein the amino group has the (S)-configuration.

Embodiment 25 relates to a compound as defined in any one of the embodiments 14-18 or a pharmaceutically acceptable salt thereof, wherein the amino group has the (R)-configuration.

Embodiment 26 relates to a compound as defined in any one of the embodiments 14-18 or a pharmaceutically acceptable salt thereof, wherein the amino group has the (S)-configuration.

Embodiment 27 relates to a compound of formula (I) in accordance to embodiment 1 or a pharmaceutically acceptable salt thereof, which is a compound of formula (V) or a pharmaceutically acceptable salt thereof;

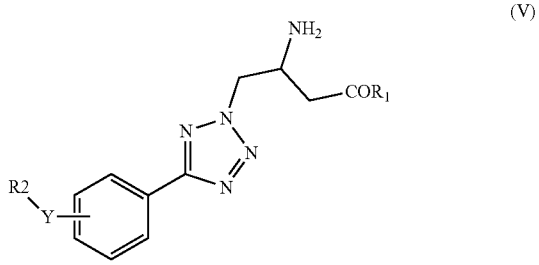

(V)

wherein the variables R1, R2 and Y have the meaning as defined in embodiment 1; or
wherein is R1 is OH; Y is O; and
R2 is phenyl optionally being substituted by halogen, $C_1$-$C_6$ alkyl, $C_1$-$C_6$ alkoxy.

Embodiment 28 relates to a compound of embodiment 27 or a pharmaceutically acceptable salt thereof;
wherein Y is in para-position.

Embodiment 29 relates to a compound of embodiment 28 or a pharmaceutically acceptable salt thereof;
wherein the primary amino group in the butanoyl-side-chain attached to the tetrazol-moiety of formula (V) has the (S)-configuration.

Embodiment 30 relates to a compound of embodiment 28 or a pharmaceutically acceptable salt thereof;
wherein the primary amino group in the butanoyl-side-chain attached to the tetrazol-moiety of formula (V) has the (R)-configuration.

Embodiment 31 relates to a compound of formula (I) and/or a pharmaceutically acceptable salt thereof in accordance to embodiment 1, wherein the compound is selected from:
(R)-3-amino-4-(5-(4-(benzo[d]thiazol-2-yloxy)phenyl)-2H-tetrazol-2-yl)butanoic acid;
(R)-3-amino-4-(5-(4-((5-chloropyridin-2-yl)oxy)phenyl)-2H-tetrazol-2-yl)butanoic acid;
(R)-3-amino-4-(5-(4-((5-chloro-3-fluoropyridin-2-yl)oxy)phenyl)-2H-tetrazol-2-yl)butanoic acid;
(R)-3-amino-4-(5-(4-(4-(oxazol-2-yl)-phenoxy)phenyl)-2H-tetrazol-2-yl)-butanoic acid;
(R)-3-amino-4-(5-(3-(4-chlorophenoxy)phenyl)-2H-tetrazol-2-yl)butanoic acid;
(R)-3-amino-4-(5-(4-(4-chlorophenoxy)-phenyl)-2H-tetrazol-2-yl)butanoic acid;
(R)-3-amino-4-(5-(4-(4-fluorophenoxy)-phenyl)-2H-tetrazol-2-yl)butanoic acid;
(R)-3-amino-4-(5-(4-(3-chloro-4-fluorophenoxy)phenyl)-2H-tetrazol-2-yl)butanoic acid;
(R)-3-amino-4-(5-(4-(p-tolyloxy)phenyl)-2H-tetrazol-2-yl)butanoic acid;
(S)-3-amino-4-(5-(3-phenoxyphenyl)-2H-tetrazol-2-yl)butanoic acid;
(S)-3-amino-4-(5-(4-(benzo[d]thiazol-2-yloxy)phenyl)-2H-tetrazol-2-yl)butanoic acid;
(S)-3-amino-4-(5-(4-(4-chlorophenoxy)-phenyl)-2H-tetrazol-2-yl)butanoic acid;
(R)-3-amino-4-(5-(3-phenethoxyphenyl)-2H-tetrazol-2-yl)butanoic acid;
(R)-3-amino-4-(5-(4-phenethoxyphenyl)-2H-tetrazol-2-yl)butanoic acid;
(R)-3-amino-4-(5-(4-(benzyloxy)phenyl)-2H-tetrazol-2-yl)butanoic acid;
(R)-3-amino-4-(5-(3-(benzyloxy)phenyl)-2H-tetrazol-2-yl)butanoic acid;
(R)-3-amino-4-(5-(4-butoxyphenyl)-2H-tetrazol-2-yl)butanoic acid;
(R)-3-amino-4-(5-(4-(pentyloxy)phenyl)-2H-tetrazol-2-yl)butanoic acid;
(R)-3-amino-4-(5-(3-((5-(trifluoromethyl)pyridin-2-yl)oxy)phenyl)-2H-tetrazol-2-yl)butanoic acid;
(R)-3-amino-4-(5-(4-((5-(trifluoromethyl)pyridin-2-yl)oxy)phenyl)-2H-tetrazol-2-yl)butanoic acid;
(R)-3-amino-4-(5-(3-(benzo[d]thiazol-2-yloxy)phenyl)-2H-tetrazol-2-yl)butanoic acid;
(R)-3-amino-4-(5-(3-(3,5-difluorophenoxy)phenyl)-2H-tetrazol-2-yl)butanoic acid;
(S)-3-amino-4-(5-(4-(p-tolyloxy)phenyl)-2H-tetrazol-2-yl)butanoic acid;
(R)-3-amino-4-(5-(4-(4-fluorophenoxy) phenyl)-1,3,4-oxadiazol-2-yl)butanoic acid;

(R)-3-amino-4-(5-(4-(4-chlorophenoxy) phenyl)-1,3,4-oxa-
diazol-2-yl)butanoic acid;
(R)-3-amino-4-(3-(4-(4-chlorophenoxy)phenyl)-1,2,4-oxa-
diazol-5-yl)butanoic acid;
(R)-3-amino-4-(3-(4-(4-chlorophenoxy)phenyl)-1,2,4-oxa-
diazol-5-yl)butanamide;
(S)-3-amino-4-(4-(4-(4-chlorophenoxy)phenyl)-1H-pyra-
zol-1-yl)butanoic acid; and
(S)-3-amino-4-(5-(4-((5-chloro-3-fluoropyridin-2-yl)oxy)
phenyl)-2H-tetrazol-2-yl)butanoic acid.

Embodiment 32 relates to a pharmaceutical composition comprising a therapeutically effective amount of a compound according to any one of embodiments 1 to 31 and one or more pharmaceutically acceptable carriers.

Embodiment 33 relates to a combination comprising a therapeutically effective amount of a compound according to any one of embodiments 1 to 31 or a pharmaceutically acceptable salt thereof and one or more therapeutically active co-agents.

Embodiment 34 relates to a method of modulating LTA4H activity in a subject, wherein the method comprises administering to the subject a therapeutically effective amount of the compound according to any one of embodiments 1 to 31 or a pharmaceutically acceptable salt thereof.

Embodiment 35 relates to a compound according to any one of embodiments 1 to 31 or a pharmaceutically acceptable salt thereof, for use as a medicament, in particular for inhibiting LTA4H activity.

Embodiment 36 relates to a compound of embodiment 27 or a pharmaceutically acceptable salt thereof; wherein
R2 is a 5-10 membered mono- or bicyclic heteroaryl containing 1 to 4 heteroatoms selected from N, O and S said heteroaryl being optionally substituted by $C_1$-$C_6$ alkyl optionally substituted by halogen, cyano or halogen.

Embodiment 37 relates to a compound of embodiment 36 or a pharmaceutically acceptable salt thereof; wherein Y is in para-position.

Embodiment 38 relates to a compound of embodiment 37 or a pharmaceutically acceptable salt thereof; wherein the primary amino group in the butanoyl-side-chain attached to the tetrazol-moiety of formula (V) has the (S)-configuration.

Embodiment 39 relates to a compound of embodiment 37 or a pharmaceutically acceptable salt thereof; wherein the primary amino group in the butanoyl-side-chain attached to the tetrazol-moiety of formula (V) has the (R)-configuration.

Embodiment 40 relates to a compound of embodiment 27 or a pharmaceutically acceptable salt thereof; wherein
R1 is OH; Y is O; and R2 is a pyridyl ring being optionally substituted by cyano or halogen.

Definitions

As used herein, the term "$C_1$-$C_6$ alkyl" refers to a fully saturated branched or unbranched hydrocarbon moiety having up to 6 carbon atoms. Unless otherwise provided, it refers to hydrocarbon moieties having 1 to 6 carbon atoms, 1 to 4 carbon atoms or 1 to 2 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl and the like.

As used herein, the term "$C_1$-$C_6$ alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1 to 6 carbon atoms, 1 to 4 carbon atoms or 1 to 2 carbon atoms.

As used herein, the term "$C_1$-$C_6$ alkyl optionally substituted by halogen" refers to $C_1$-$C_6$ alkyl as defined above which may be substituted by one or more halogens. Examples include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "di $C_{1-6}$alkylamino" refers to a moiety of the formula —N($R_a$)—$R_a$ where each $R_a$ is a $C_{1-6}$alkyl, which may be the same or different, as defined above.

As used herein, the term "$C_3$-$C_6$ cycloalkyl" refers to saturated monocyclic hydrocarbon groups of 3-6 carbon atoms. Cycloalkyl may also be referred to as a carbocyclic ring and vice versa additionally referring to the number of carbon atoms present. Unless otherwise provided, cycloalkyl refers to cyclic hydrocarbon groups having between 3 and 6 ring carbon atoms or between 3 and 4 ring carbon atoms. Exemplary monocyclic hydrocarbon groups include, but are not limited to, cyclopropyl, cyclobutyl, cyclopentyl, and cyclohexyl.

As used herein, the term "halogen" or "halo" refers to fluoro, chloro, bromo, and iodo.

As used herein, the term "heterocyclyl" refers to a heterocyclic group that is saturated or partially saturated and is preferably a monocyclic or a polycyclic ring (in case of a polycyclic ring particularly a bicyclic, tricyclic or spirocyclic ring); and has 3 to 24, more preferably 4 to 16, most preferably 5 to 10 and most preferably 5 or 6 ring atoms;
wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl excludes heteroaryl. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1, 4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-4, such as one, or two, or three, or four substituents.

As used herein, the term "heteroaryl" refers to a 5-14 membered monocyclic- or bicyclic- or tricyclic-aromatic ring system, having 1 to 8 heteroatoms. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2, 3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d] thiazolyl, 3-, 5-, or 8-pyrazino[2,3-d]pyridazinyl, 2-, 3-, 5-, or 6-imidazo[2,1-b] thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl. A substituted heteroaryl is a heteroaryl group containing one or more substituents.

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl.

A substituted aryl is an aryl group substituted by 1-5 (such as one, or two, or three) substituents independently selected from the group consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, de-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by LTA4H, or (ii) associated with LTA4H activity, or (iii) characterized by activity (normal or abnormal) of LTA4H; or (2) reducing or inhibiting the activity of LTA4H; or (3) reducing or inhibiting the expression of LTA4H. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of LTA4H; or reducing or inhibiting the expression of LTA4H partially or completely.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. For greater clarity, the term "possible isomers" shall not include positional isomers.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral stationary phase.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Methods of Synthesizing Heteroaryl Butanoic Acid Derivatives

Agents of the invention, for example compounds in accordance to the definition of formula (I), may be prepared by a reaction sequence of the reaction scheme A, involving the synthesis of the amino acid building block of formula 1, which is usually obtained by reacting the commercially available protected amino acid Boc-Asp(OtBu)—OH selectively, or after activation of the carboxylic acid group with a reducing agent, e.g. NaBH$_4$ in the presence of a solvent at low temperatures, e.g. −20° C. or the like. Depending on the stereochemistry of the starting material, (S)- or (R)-tert-butyl 3-(tert-butoxycarbonyl-amino)-4-hydroxybutanoate are obtained as chiral building blocks of formula 1. The variables in schemes A-D correspond to the definitions provided in embodiment 1. In addition, the term "PG" denotes a protecting group such as tert-butyloxy-carbonyl or Boc.

The building blocks of formula 1 may be reacted with thionylchloride in a solvent in the presence of a suitable base, e.g. imidazole which is then further reacted with an oxidative reagent, such as periodate and typically in the presence of a catalyst such as a Ruthenium halide to yield the cyclic building blocks of formula 2 optionally again as a chiral building block when chiral starting materials of formula 1 are being taken.

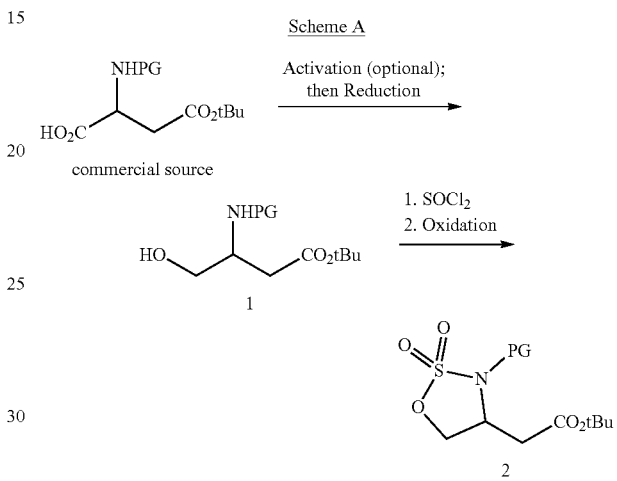

Scheme A

As a further building block for synthesizing the compounds of the invention, the so-called nitrils 3 may be obtainable by reacting commercially available substrates of the formula R2-Hal and appropriately substituted benzonitrils (Y═O) in the presence of a base, e.g. potassium carbonate in a solvent, e.g. DMF and if required at elevated temperatures, e.g. above 100° C. Alternatively, nitriles 3 may be obtained by reacting commercially available fluoro-substituted nitriles with commercially available substituted alcohols, e.g. phenols.

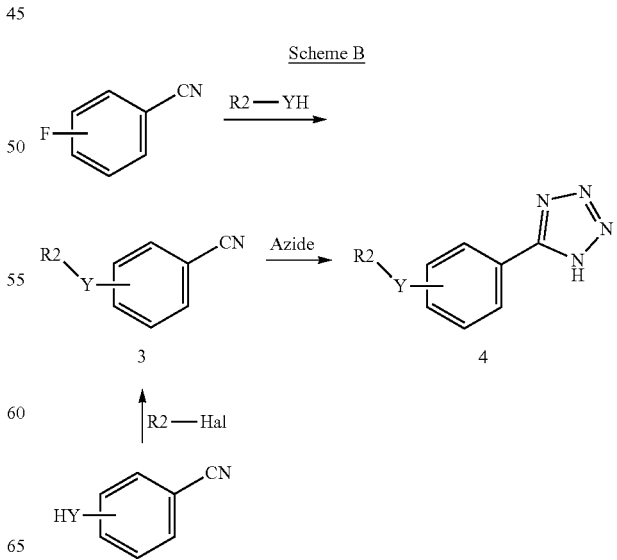

Scheme B

A nitril 3 is then typically reacted with an azide, e.g. azidotrimethylsilane and typically in the presence of a catalyst such as dibutyl tin (IV) oxide to yield a tetrazole of general formula 4, (see scheme B) which is reacted with a suitable electrophil, typically with an activated alcohol of general formula 1, e.g. mesylated or tosylated or otherwise activated, e.g in-situ under Mitsunobu conditions, or is alternatively reacted with the activated cyclic building block of general formula 2, to yield an intermediate compound of general formula 5 (scheme C). In addition to "tBu" the alkyl moiety of the Ester group in the compounds 1, 2 and 5 may alternatively be Bn, Me, or Et or another suitable protecting group.

Scheme C

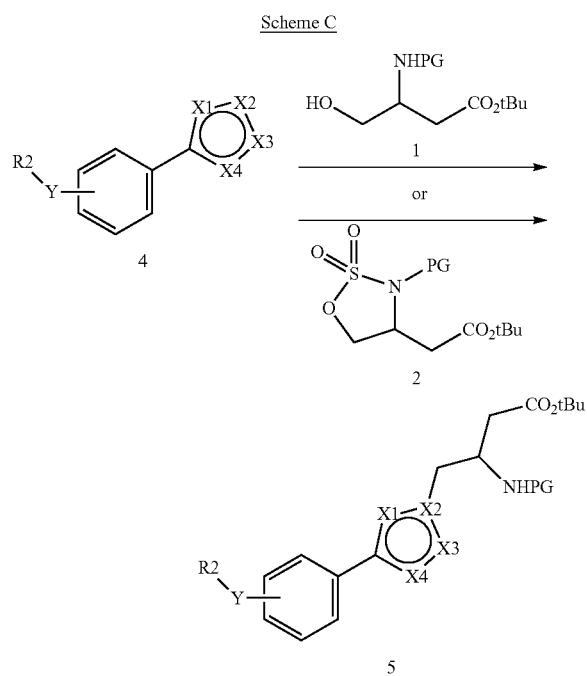

The intermediate compounds 5 are then typically reacted with an acid or a base, e.g. hydrochloric acid or TFA, or e.g. with piperidine as a base, usually in a solvent, for example dioxane or dichloromethane, to yield a compound of the invention of formula (I), R1=OH, according to scheme D. To obtain compounds with R1=NH$_2$, the ester group in formula 5 may be cleaved to give the acid, which is then activated and reacted with ammonia or an ammonia equivalent. Subsequent treatment with acid yields the amide R1=NH$_2$ in accordance to formula (I).

Scheme D

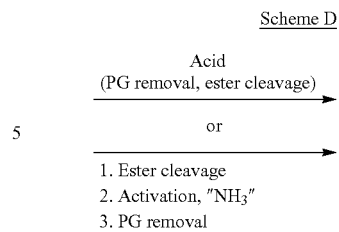

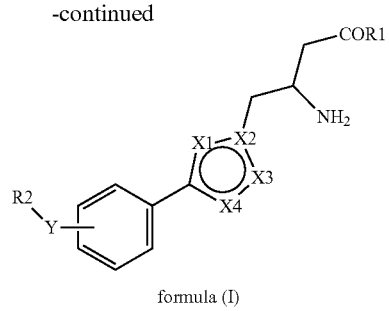

formula (I)

Alternative Routes of Synthesizing Compounds of the Invention

Depending on the nature of the building blocks or substrates that are taken as starting materials for making a compound of the invention it may be necessary to deviate from this general reaction sequence provided above. These deviations are described in detail in the following section entitled Experimental Section.

EXPERIMENTAL SECTION

Abbreviations

2-MeTHF 2-methyltetrahydrofuran
Asp aspartic acid
aq aqueous
Bn or Bzl benzyl
Boc tert-butyloxycarbonyl
br broad
brine saturated aqueous NaCl solution
d doublet
dd doublet of doublets
DCM dichloromethane
DIAD diisopropyl azodicarboxylate
DIPEA diisopropylethylamine
DME 1,2-dimethoxyethane
DMF N,N-dimethyl formamide
DMSO dimethylsulfoxide
EDC 1-ethyl-3-(3-dimethylaminopropyl)carbodiimid
ESI electrospray ionization
EtOAc ethyl acetate
EtOH ethanol
eq equivalent(s)
Ex example(s)
Fmoc fluorenylmethyloxycarbonyl
Gln glutamine
Glu glutamic acid
h hour
HATU 1-[Bis(dimethylamino)methylene]-1H-1,2,3-triazolo[4,5-b]pyridinium 3-oxid hexafluorophosphate
HOBT hydroxybenzotriazol
HPLC high performance liquid chromatography
iPrOH iso-propanol
i. vac. in vacuo
LC liquid chromatography
m multiplet/milli, depending on the context
MeOH methanol
mg milligram
min minutes
MS mass spectrometry
mL milliliter
mmol millimol
m/z mass to charge ratio NMR nuclear magnetic resonance
ppm parts per million
q quartet
quint quintet
rt room temperature
Rt retention time
s singlet
t triplet
TBAF tetrabutylammonium fluoride
TBME tert-butylmethylether
TBS tert-butyldimethylsilyl
tBu tert-butyl
TFA trifluoroacetic acid
THF tetrahydrofuran
TLC thin layer chromatography
Tos tosyl, p-toluolsulfonyl
UPLC ultra performance liquid chromatography Analytical Details NMR: Measurements were performed on a Bruker Ultrashield™ 400 (400 MHz), Bruker Ultrashield™ 600 (600 MHz), 400 MHz DRX Bruker CryoProbe (400 MHz) or a 500 MHz DRX Bruker CryoProbe (500 MHz) spectrometer using or not trimethylsilane as an internal standard. Chemical shifts (6-values) are reported in ppm downfield from tetramethylsilane, spectra splitting pattern are designated as singlet (s), doublet (d), triplet (t), quartet (q), quintet (quint), multiplet, unresolved or overlapping signals (m), broad signal (br). Deuterated solvents are given in parentheses.
Lc-Ms:
UPLC-MS Conditions a:
  System: Waters Acquity UPLC with Waters SQ detector.
  Column: Acquity HSS T3 1.8 µm 2.1×50 mm, column temperature: 60° C.
  Gradient: from 5 to 98% B in 1.4 min, A=water+0.05% formic acid+3.75 mM ammonium acetate, B=acetonitrile+0.04% formic acid, flow: 1.0 mL/min.
UPLC-MS Conditions b:
  System: Waters Acquity UPLC with Waters SQ detector.
  Column: Acquity HSS T3 1.8 µm 2.1×50 mm, column temperature: 60° C.
  Gradient: from 5 to 98% B in 9.4 min, A=water+0.05% formic acid+3.75 mM ammonium acetate, B=acetonitrile+0.04% formic acid, flow: 1.0 mL/min.
HPLC Conditions c:
  System: Jasco LC-2000 Series with MD-2015 detector.
  Column: Chiracel OZ 5 µm 5×250 mm, column temperature: rt.
  85% heptane, 15% iPrOH+0.05% TFA, flow: 1 mL/min.
HPLC Conditions d:
  System: Jasco LC-2000 Series with MD-2015 detector.
  Column: Chiralpak IC 5 µm 5×250 mm, column temperature: rt.
  60% heptane, 40% EtOH+0.1% TFA, flow: 0.5 mL/min.
HPLC Conditions e:
  System: Jasco LC-2000 Series with MD-2015 detector.
  Column: Chiralpak IC 5 µm 5×250 mm, column temperature: rt.
  50% heptane, 50% EtOH+0.1% TFA, flow: 0.5 mL/min.
HPLC Conditions f:
  System: Agilent 1200 Series with DAD detector.
  Column: Chiralpak AD-H 5 µm 4.6×250 mm, column temperature: rt.
  60% heptane, 40% EtOH, flow: 0.7 mL/min.
HPLC Conditions q:
  System: Jasco LC-2000 Series with MD-2015 detector.
  Column: Chiralpak IC 5 µm 5×250 mm, column temperature: rt.
  85% heptane, 12% iPrOH, 3% EtOH+0.1% TFA, flow: 0.5 mL/min.
HPLC Conditions h:
  System: Agilent 1100 Series with DAD detector.
  Column: Chiralpak IC 5 µm 5×250 mm, column temperature: rt.
  80% heptane, 10% EtOH, 10% MeOH+0.1% HNEt$_2$+0.1% TFA, flow: 1.0 mL/min.

Preparative Methods

Flash Chromatography System:
  System: Teledyne ISCO, CombiFlash Rf.
  Column: pre-packed RediSep Rf cartridges.
  Samples were typically adsorbed on Isolute.
  All reagents, starting materials and intermediates utilized in these examples were available from commercial sources or were readily prepared by methods known to those skilled in the art.

Synthesis of the Amino Acid Derived Building Blocks

Alcohols 1a-1d were prepared by a method similar to that described by J. Martinez et al, Tetrahedron Letters 1991, 32, 923-926.

(S)-tert-butyl 3-((tert-butoxycarbonyl)amino)-4-hydroxybutanoate (1a)

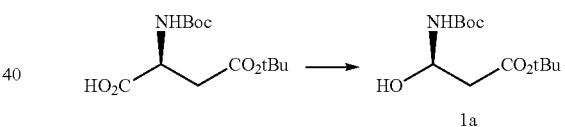

To a cold solution of Boc-L-Asp(OtBu)—OH (25.0 g, 86.0 mmol) in DME (86 mL) were successively added N-methylmorpholine (10.1 mL, 90.0 mmol) and isobutyl chloroformate (12.2 mL, 91.0 mmol) at such a rate that the temperature stayed below −10° C. After 30 min, the precipitated N-methyl morpholine hydrochloride was removed by filtration, washed with DME (25 mL) and the filtrate and washings were combined in a flask in an ice-salt bath. A solution of NaBH$_4$ (4.14 g, 108 mmol) in water (30 mL) was added slowly, followed by water (70 mL) maintaining the temperature between −15° C. and −30° C. The suspension was filtered and washed thoroughly with water. The filtrate was extracted with EtOAc (4×50 mL) and the combined organic layers were washed with brine, dried over Na$_2$SO$_4$ and concentrated under reduced pressure. The crude product was purified by flash column chromatography on silica (heptane:EtOAc 1:0 to 1:1) affording the title compound as a thick oil that slowly solidified.

M/z=276.2 [M+H]$^+$, Rt=3.04 min (UPLC-MS conditions b), Rt=6.83 min (HPLC conditions g), $^1$H NMR (400 MHz, CDCl$_3$) δ=5.22 (s, br, 1H), 3.87-4.03 (m, 1H), 3.68 (d, 2H), 2.39-2.63 (m, 2H), 1.35-1.54 (m, 18H) ppm.

Alcohols 1b-d were prepared in analogy to alcohol 1a.

| Structure and Name | Reaction Parameter | Analytics |
|---|---|---|
| 1a ![structure] HO~~~CO₂tBu with NHBoc (wedge) <br> (S)-tert-butyl 3-((tert-butoxycarbonyl)amino)-4-hydroxybutanoate | See above | See above |
| 1b HO~~~CO₂tBu with NHBoc (dash) <br> (R)-tert-butyl 3-((tert-butoxycarbonyl)amino)-4-hydroxybutanoate | Starting from Boc-D-Asp(OtBu)-OH | M/z = 276.1 [M + H]⁺, Rt = 3.11 min (UPLC-MS conditions b), Rt = 8.67 min (HPLC conditions g), ¹H NMR (400 MHz, CDCl₃) δ = 5.27 (s, br, 1H), 3.88-4.02 (m, 1H), 3.68 (d, 2H), 2.41-2.65 (m, 2H), 1.30-1.52 (m, 18H) ppm. |
| 1c HO~~~CO₂Bn with NHBoc (wedge) <br> (S)-benzyl 3-((tert-butoxycarbonyl)amino)-4-hydroxybutanoate | Starting from Boc-L-Asp(OBzl-OH; Filtering the reaction mixture afforded the solid product that was thoroughly washed with water and dried i. vac. | M/z = 310.1 [M + H]⁺, Rt = 3.39 min (UPLC-MS conditions b), Rt = 6.33 min (HPLC conditions f), ¹H NMR (400 MHz, MeOD-d₄) δ = 7.24-7.43 (m, 5H), 5.12 (s, 2H), 3.99 (dd, 1H), 3.41-3.61 (m, 2H), 2.67 (dd, 1H), 2.50 (dd, 1H), 1.42 (s, 9H) ppm. |
| 1d HO~~~CO₂Bn with NHBoc (dash) <br> (R)-benzyl 3-((tert-butoxycarbonyl)amino)-4-hydroxybutanoate | Starting from Boc-D-Asp(OBzl-OH; Filtering the reaction mixture afforded the solid product that was thoroughly washed with water and dried i. vac. | M/z = 310.4 [M + H]⁺, Rt = 3.33 min (UPLC-MS conditions b), Rt = 8.46 min (HPLC conditions f), ¹H NMR (400 MHz, MeOD-d₄) δ = 7.26-7.41 (m, 5H), 5.12 (s, 2H), 3.93-4.01 (m, 1H), 3.51-3.58 (m, 1H), 3.42-3.50 (m, 1H), 2.67 (dd, 1H), 2.50 (dd, 1H), 1.42 (s, 9H) ppm. |

Sulfamidates 2a and 2b were prepared by a method similar to that described by A. G. Jamieson et al, Journal of the American Chemical Society 2009, 131, 7917-7927.

(S)-tert-butyl 4-(2-(tert-butoxy)-2-oxoethyl)-1,2,3-oxathiazolidine-3-carboxylate 2,2-dioxide (2a)

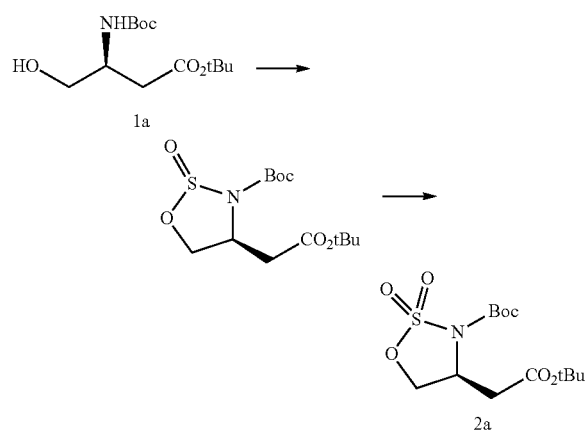

Step 1: A solution of imidazole (16.0 g, 235 mmol) in 2-MeTHF (150 mL) was cooled to −78° C. resulting in a colorless suspension. Thionylchloride (4.29 mL, 58.8 mmol) was added dropwise. After 10 min, (S)-tert-butyl 3-((tert-butoxycarbonyl)amino)-4-hydroxybutanoate (1a, 6.0 g, 19.6 mmol) in 2-MeTHF (30 mL) was added dropwise. The cooling was removed and the RM was stirred for 2 h at rt, before it was filtered over a pad of Celite™. All volatiles were removed i. vac. and the residue was partitioned between DCM (100 mL) and water (100 mL). The aqueous phase was extracted with DCM (2×50 mL) and the combined organic layers were washed with aq. HCl (10%, 20 mL) and brine (20 mL), dried (MgSO₄) and concentrated.

Step 2: The residue was dissolved in MeCN (100 mL), cooled to 0° C., and treated with portions of solid RuCl₃ monohydrate (177 mg, 0.784 mmol) and NaIO₄ (6.29 g, 29.4 mmol), followed by dropwise addition of water (50 mL). After stirring at 0° C. for 2 h, the reaction mixture was partitioned between EtOAc (100 mL) and water (20 mL). The aqueous phase was extracted with EtOAc (2×50 mL) and the combined organic layers were washed with sat. NaHCO₃ (50 mL) and brine (50 mL). The grey organic phase was filtered successively over plugs of Celite™, Na₂SO₄ and silica until clear and colorless. Removal of all volatiles i. vac. afforded the title compound 2a as a colorless solid.

¹H NMR (400 MHz, CDCl₃) δ=4.77 (dd, 1H), 4.56-4.64 (m, 1H) 4.53 (dd, 1H), 3.02 (dd, 1H), 2.76 (dd, 1H), 1.58 (s, 9H), 1.48 (s, 9H) ppm.

(R)-tert-butyl 4-(2-(tert-butoxy)-2-oxoethyl)-1,2,3-oxathiazolidine-3-carboxylate 2,2-dioxide (2b)

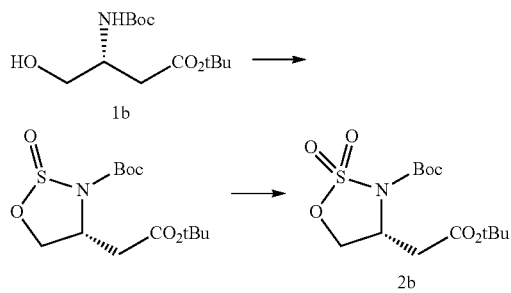

Sulfamidate 2b was prepared in analogy to 2a starting from alcohol 1b.

$^1$H NMR (400 MHz, CDCl$_3$) δ=4.78 (dd, 1H), 4.56-4.63 (m, 1H) 4.52 (dd, 1H), 3.02 (dd, 1H), 2.77 (dd, 1H), 1.58 (s, 9H), 1.48 (s, 9H) ppm.

Synthesis of the Nitrile Intermediates

4-(benzo[d]thiazol-2-yloxy)benzonitrile (3a)

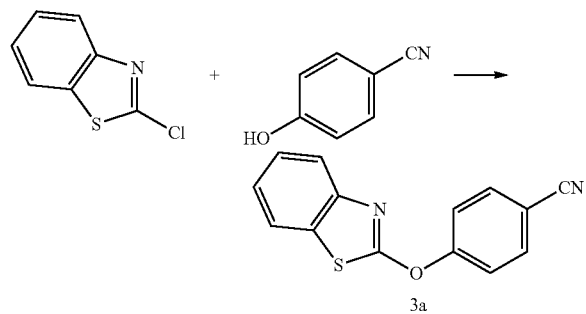

A suspension of 4-hydroxybenzonitrile (6.55 g, 55.0 mmol), 2-chlorobenzothiazole (6.51 mL, 50.0 mmol) and K$_2$CO$_3$ (7.60 g, 55.0 mmol) in DMF (20 mL) was heated to 120° C. for 18 h. The reaction mixture was cooled to rt, diluted with heptane:EtOAc (1:1, 300 mL) and washed with 0.2 N NaOH (200 mL), sat. Na$_2$CO$_3$ (50 mL) and brine (50 mL). Drying over Na$_2$SO$_4$, filtering and concentration to dryness afforded a crude product which was purified by crystallization (heptane:EtOAc) to yield the desired ether 3a as a beige solid.

M/z=253.1 [M+H]$^+$, Rt=1.13 min (UPLC-MS conditions a), $^1$H NMR (400 MHz, DMSO-d$_6$) δ=7.98-8.05 (m, 3H), 7.69-7.75 (m, 3H), 7.46 (dd, 1H), 7.38 (dd, 1H) ppm.

4-((5-chloropyridin-2-yl)oxy)benzonitrile (3b)

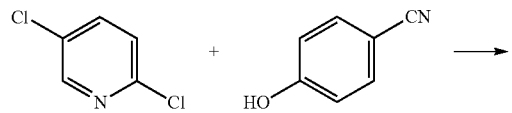

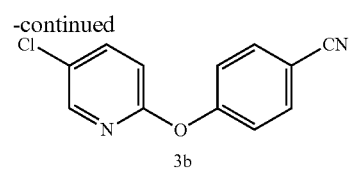

Nitrile 3b was prepared in analogy to nitrile 3a starting from 2,5-dichloropyridine and 4-hydroxybenzonitrile and obtained after tituration with MeOH as a colorless solid.

M/z=230.9 [M+H]$^+$, Rt=1.07 min (UPLC-MS conditions a), $^1$H NMR (400 MHz, DMSO-d$_6$) δ=8.26 (d, 1H), 8.05 (dd, 1H), 7.91 (d, 2H), 7.36 (d, 2H), 7.24 (d, 1H) ppm.

4-((5-chloro-3-fluoropyridin-2-yl)oxy)benzonitrile (3c)

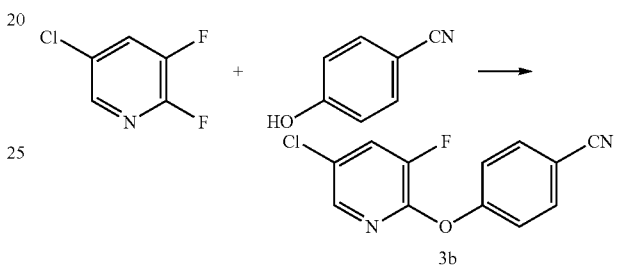

Nitrile 3c was prepared in analogy to nitrile 3a starting from 5-chloro-2,3-difluoropyridine and 4-hydroxybenzonitrile at 90° C. reaction temperature. The title compound was obtained as a colorless solid containing ca. 7% of a side-product that was carried forward into the next step and removed there.

M/z=249.2 [M+H]$^+$, Rt=1.10 min (UPLC-MS conditions a), $^1$H NMR (400 MHz, DMSO-d$_6$) δ=8.30 (dd, 1H), 8.13 (dd, 1H), 7.93 (d, 2H), 7.43 (d, 2H) ppm, $^{19}$F NMR (376 MHz, DMSO-d$_6$) δ=−133.7 (d, 1F) ppm.

4-(4-(oxazol-2-yl)phenoxy)benzonitrile (3d)

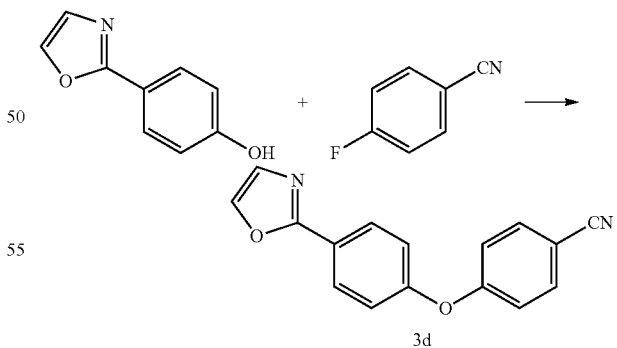

A suspension of 4-(oxazol-2-yl)phenol (200 mg, 1.24 mmol), 4-fluorobenzonitrile (301 mg, 2.48 mmol) and K$_2$CO$_3$ (515 mg, 3.72 mmol) in DMF (1.2 mL) was heated to 100° C. for 16 h. The reaction mixture was concentrated i. vac. and purified by flash column chromatography on RP18 silica (0.1% TFA in water:MeCN from 9:1 to 0:1) to afford the title compound 3d as a colorless powder.

M/z=263.1 [M+H]⁺, Rt=1.07 min (UPLC-MS conditions a), $^1$H NMR (400 MHz, DMSO-d$_6$) δ=8.23 (s, 1H), 8.06 (d, 2H), 7.90 (d, 2H), 7.39 (s, 1H), 7.28 (d, 2H), 7.23 (d, 2H) ppm.

Synthesis of the Tetrazole Intermediates

Compounds of the invention were typically synthesized via intermediates of formula 4a-formula 4o (see also reaction schemes B and C). In the following these compounds were usually displayed in one tautomeric form, e.g. the 1H-tetrazol-5-yl. Likewise the corresponding chemical names of said intermediates were provided for one tautomeric form only. However, such a tautomer may also exist in another tautomeric form, e.g. as 2H-tetrazol-5-yl tautomer. Hence any tautomeric form may be encompassed in an intermediate of formula 4 (4a-4o) even if only one particular form has been shown. 2-(4-(1H-tetrazol-5-yl)phenoxy)benzo[d]thiazole (4a)

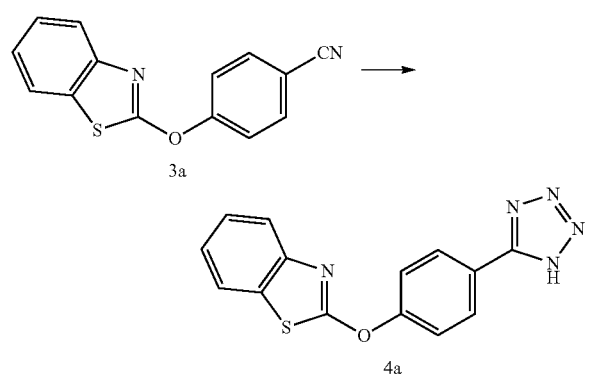

A suspension of 4-(benzo[d]thiazol-2-yloxy)benzonitrile (3a, 1.51 g, 6.00 mmol) and dibutyltin (IV) oxide (0.149 g, 0.600 mmol) in dry toluene (9.0 mL) was flushed with argon. Azidotrimethylsilane (1.59 mL, 12.0 mmol) was added before the vial was sealed and heated to 110° C. for 8 h. The reaction mixture was cooled to rt, treated with MeOH (5 mL) and concentrated i. vac. Washing with MeCN (50 mL) and pentane (15 mL) afforded the desired tetrazole 4a as a beige solid.

M/z=296.1 [M+H]⁺, Rt=0.91 min (UPLC-MS conditions a), $^1$H NMR (400 MHz, DMSO-d$_6$) δ=16.6-17.3 (s, br, 1H), 8.17 (d, 2H), 7.99 (d, 1H), 7.70-7.76 (m, 3H), 7.46 (d, 1H), 7.37 (d, 1H) ppm.

5-(4-(4-chlorophenoxy)phenyl)-1H-tetrazole (4f)

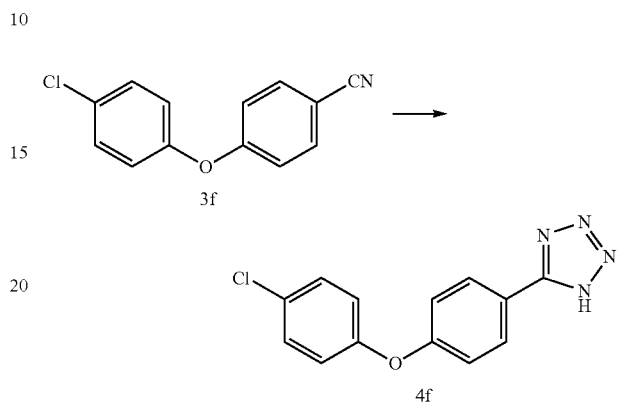

A suspension of 4-(4-chlorophenoxy) benzonitrile (3f, 1.43 g, 6.23 mmol) and dibutyltin (IV) oxide (0.155 g, 0.623 mmol) in dry toluene (9.0 mL) was flushed with argon. Azidotrimethylsilane (1.65 mL, 12.5 mmol) was added before the vial was sealed and heated to 100° C. for 17 h. The reaction mixture was cooled to rt, treated with MeOH (6 mL) and concentrated i. vac. Washing with MeCN (15 mL) and heptane (15 mL) afforded the desired tetrazole 4f as a colorless solid.

M/z=273.0 [M+H]⁺, Rt=0.99 min (UPLC-MS conditions a), $^1$H NMR (400 MHz, DMSO-d$_6$) δ=16.8 (s, br, 1H), 8.06 (d, 2H), 7.50 (d, 2H), 7.23 (d, 2H), 7.17 (d, 2H) ppm.

Further tetrazoles, e.g. the tetrazoles 4b-j were prepared in analogy to tetrazole 4a. The reaction parameters and the analytics (characterization of compound) are provided in the following table.

| | Structure and Name | Reaction Parameter | Analytics |
|---|---|---|---|
| 4a | 2-(4-(1H-tetrazol-5-yl)phenoxy)benzo[d]thiazole | See above | See above |
| 4b | 2-(4-(1H-tetrazol-5-yl)phenoxy)-5-chloropyridine | 100° C., 16 h | M/z = 274.0 [M + H]⁺, Rt = 0.85 min (UPLC-MS conditions a), $^1$H NMR (400 MHz, DMSO-d$_6$) δ = 16.8 (s, br, 1H), 8.25 (d, 1H), 8.09 (d, 2H), 8.02 (d, 1H), 7.39 (d, 2H), 7.22 (d, 1H) ppm. |

-continued

| | Structure and Name | Reaction Parameter | Analytics |
|---|---|---|---|
| 4c | 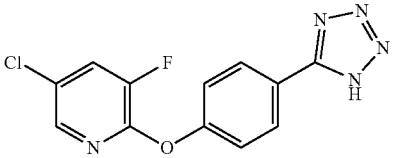 [SMILES: Fc1cc(Cl)cnc1Oc1ccc(-c2nnn[nH]2)cc1]<br>2-(4-(1H-tetrazol-5-yl)-phenoxy)-5-chloro-3-fluoropyridine | 100° C., 18 h | M/z = 292.1 [M + H]$^+$, Rt = 0.88 min (UPLC-MS conditions a), $^1$H NMR (400 MHz, DMSO-d$_6$) δ = 16.8 (s, br, 1H), 8.28 (dd, 1H), 8.08-8.13 (m, 3H), 7.43 (d, 2H) ppm, $^{19}$F NMR (376 MHz, DMSO-d$_6$) δ = −134.03 (s, 1F) ppm. |
| 4d | 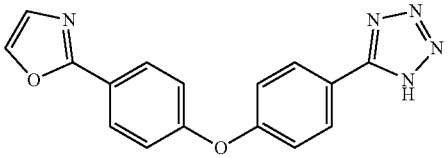 [SMILES: c1coc(-c2ccc(Oc3ccc(-c4nnn[nH]4)cc3)cc2)n1]<br>2-(4-(4-(1H-tetrazol-5-yl) phenoxy)phenyl)oxazole | 100° C., 18 h; flash column chromatography on RP18 silica (0.1% TFA in water:MeCN from 9:1 to 0:1) | M/z = 306.1 [M + H]$^+$, Rt = 0.87 min (UPLC-MS conditions a). |
| 4e | 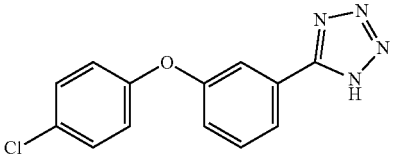 [SMILES: Clc1ccc(Oc2cccc(-c3nnn[nH]3)c2)cc1]<br>5-(3-(4-chlorophenoxy)-phenyl)-1H-tetrazole | 100° C., 18 h; flash column chromatography on RP18 silica (0.1% TFA in water:MeCN from 9:1 to 0:1) | M/z = 273.0 [M + H]$^+$, Rt = 0.99 min (UPLC-MS conditions a). |
| 4f | 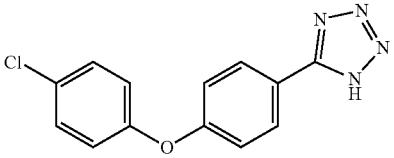 [SMILES: Clc1ccc(Oc2ccc(-c3nnn[nH]3)cc2)cc1]<br>5-(4-(4-chlorophenoxy)-phenyl)-1H-tetrazole | See above | See above |
| 4g | 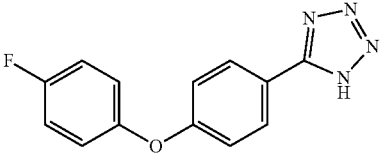 [SMILES: Fc1ccc(Oc2ccc(-c3nnn[nH]3)cc2)cc1]<br>5-(4-(4-fluorophenoxy)-phenyl)-1H-tetrazole | 100° C., 16 h | M/z = 257.1 [M + H]$^+$, Rt = 0.92 min (UPLC-MS conditions a), $^1$H NMR (400 MHz, DMS0-d$_6$) δ = 16.9 (s, br, 1H), 8.04 (d, 2H), 7.25-7.34 (m, 2H), 7.15-7.23 (m, 4H) ppm. |
| 4h | 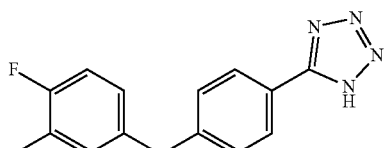<br>5-(4-(3-chloro-4-fluoro-phenoxy)phenyl-1H-tetrazole | 90° C., 20 h; flash column chromatography on RP18 silica (0.1% TFA in water:MeCN from 9:1 to 0:1) | M/z = 291.0 [M + H]$^+$, Rt = 0.99 min (UPLC-MS conditions a). |

| Structure and Name | Reaction Parameter | Analytics |
|---|---|---|
| 4i ![5-(4-(p-tolyloxy)phenyl)-1H-tetrazole] 5-(4-(p-tolyloxy)phenyl)-1H-tetrazole | 100° C., 18 h | M/z = 253.1 [M + H]+, Rt = 1.00 min (UPLC-MS conditions a), 1H NMR (400 MHz, DMSO-d6) δ = 16.75 (s, br, 1H), 8.02 (d, 2H), 7.26 (d, 2H), 7.14 (d, 2H), 7.03 (d, 2H), 2.32 (s, 3H) ppm. |
| 4j ![5-(3-phenoxyphenyl)-1H-tetrazole] 5-(3-phenoxyphenyl)-1H-tetrazole | 100° C., 18 h; flash column chromatography on silica (heptane:EtOAc from 1:0 to 1:1) | M/z = 239.1 [M + H]+, Rt = 0.90 min (UPLC-MS conditions a), 1H NMR (400 MHz, DMSO-d6) δ = 16.95 (s, br, 1H), 7.81 (d, 1H), 7.61-7.65 (m, 2H), 7.42-7.47 (m, 2H), 7.21-7.25 (m, 2H), 7.12 (d, 2H) ppm. |

Synthesis of the Substituted Tetrazole Intermediates

Method A: (R)-tert-butyl 4-(5-(4-(benzo[d]thiazol-2-yloxy)phenyl)-2H-tetrazol-2-yl)-3-((tert-butoxycarbonyl)amino)butanoate (5a)

Method B: (R)-3-((tert-butoxycarbonyl)amino)-4-(5-(4-(4-chlorophenoxy)phenyl)-2H-tetrazol-2-yl)butanoic acid (5f)

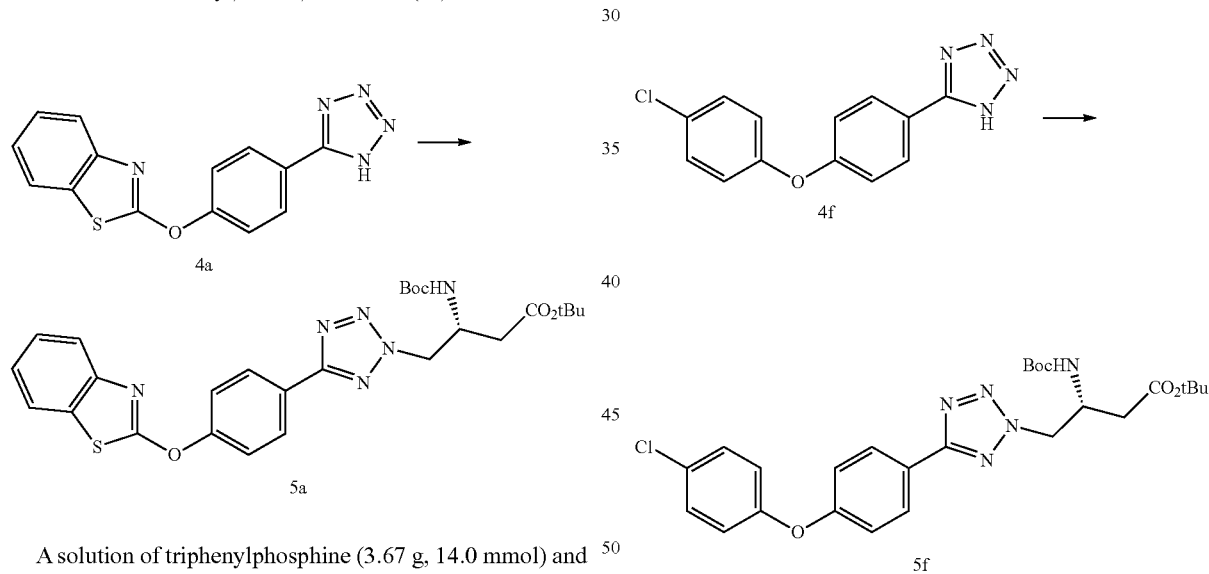

A solution of triphenylphosphine (3.67 g, 14.0 mmol) and DIAD (1.70 mL, 8.75 mmol) in THF (10 mL) was cooled to 0° C. before it was slowly transferred to a stirred suspension of 2-(4-(1H-tetrazol-5-yl)phenoxy)benzo[d]thiazole (4a, 2.07 g, 7.00 mmol) and (R)-tert-butyl 3-((tert-butoxycarbonyl)amino)-4-hydroxybutanoate (1b, 2.12 g, 7.70 mmol) in THF (10 mL). After 1 h at rt, the reaction mixture was concentrated i. vac. The crude product was purified by flash column chromatography on RP18 silica (0.1% TFA in water:MeCN from 9:1 to 0:1) to afford the title compound 5a as an orange oil.

M/z=553.3 [M+H]+, Rt=6.28 min (UPLC-MS conditions b), 1H NMR (400 MHz, DMSO-d6) δ=8.17 (d, 2H), 7.98 (d, 1H), 7.73 (d, 1H), 7.67 (d, 2H), 7.45 (t, 1H), 7.36 (t, 1H), 7.02 (d, 1H), 4.86 (dd, 1H), 4.66 (dd, 1H), 4.26-4.37 (m, 1H), 2.65 (dd, 1H), 2.41-2.54 (m, 1H), 1.41 (s, 9H), 1.25 (s, 9H) ppm.

A solution of triphenylphosphine (5.77 g, 22.0 mmol) and DIAD (2.67 mL, 13.8 mmol) in 2-MeTHF (20 mL) was cooled to 0° C. before it was slowly transferred to a stirred suspension of 5-(4-(4-chlorophenoxy)phenyl)-1H-tetrazole (4f, 3.00 g, 11.0 mmol) and (R)-benzyl 3-((tert-butoxycarbonyl)amino)-4-hydroxybutanoate (1d, 3.74 g, 12.1 mmol) in 2-MeTHF (20 mL). After 30 min at rt, 2 N NaOH (45.8 mL, 92 mmol) was added and the resulting suspension was heated to 80° C. for 30 min. The reaction mixture was diluted with heptane:EtOAc (1:1, 400 mL) and extracted with 1 N NaOH (9×100 mL). The combined aqueous extracts were carefully acidified to pH=3 using conc. HCl and extracted with EtOAc (3×150 mL). The combined organic extracts were dried over Na2SO4, filtered and concentrated i. vac. The crude product was purified by crystallization (heptane:EtOAc) to yield the desired acid 5f as a colorless solid.

M/z=474.2 [M+H]$^+$, Rt=5.09 min (UPLC-MS conditions b), Rt=8.51 min (HPLC conditions c), $^1$H NMR (400 MHz, DMSO-d$_6$) δ=12.4 (s, 1H), 8.06 (d, 2H), 7.49 (d, 2H), 7.19 (d, 2H), 7.15 (d, 2H), 6.99 (d, 1H), 4.86 (dd, 1H), 4.66 (dd, 1H), 4.23-4.33 (m, 1H), 2.61 (dd, 1H), 2.47-2.54 (m, 1H), 1.24 (s, 9H) ppm.

Method C: (S)-tert-butyl 3-((tert-butoxycarbonyl)amino)-4-(5-(4-(4-chlorophenoxy)phenyl)-2H-tetrazol-2-yl)butanoate (5m)

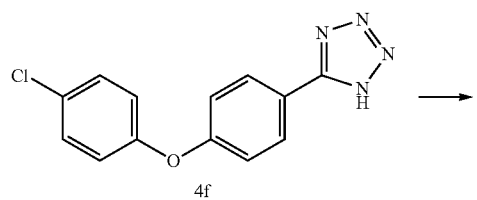

4f

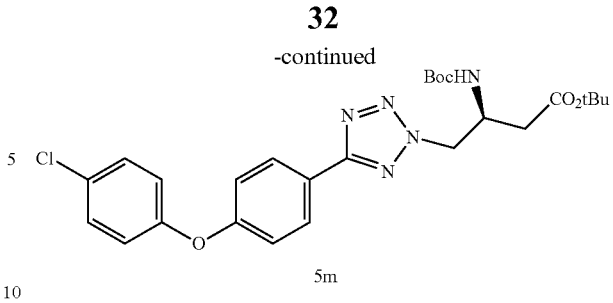

5m

A solution of 5-(4-(4-chlorophenoxy)phenyl)-1H-tetrazole (4f, 200 mg, 0.733 mmol) and (S)-tert-butyl 4-(2-(tert-butoxy)-2-oxoethyl)-1,2,3-oxathiazolidine-3-carboxylate 2,2-dioxide (2a, 330 mg, 0.880 mmol) in DMF (5 mL) was treated with DIPEA (0.384 mL, 2.20 mmol) and stirred at rt for 18 h. The reaction mixture was concentrated i. vac. and the residue was purified by flash column chromatography on RP18 silica (0.1% TFA in water:MeCN from 9:1 to 0:1) to afford the title compound 5m as a colorless semisolid. M/z=530.2 [M+H]$^+$, Rt=6.69 min (UPLC-MS conditions b), $^1$H NMR (400 MHz, MeOD-d$_4$) δ=8.13 (d, 2H), 7.42 (d, 2H), 7.15 (d, 2H), 7.08 (d, 2H), 4.89 (dd, 1H), 4.76 (dd, 1H), 4.45-4.53 (m, 1H), 2.67 (dd, 1H), 2.53 (dd, 1H), 1.49 (s, 9H), 1.34 (s, 9H) ppm.

Alkylation products 5b-l were prepared in analogy to 5a, 5f or 5m

| | Structure and Name | Reaction Parameter | Analytics |
|---|---|---|---|
| 5a | (R)-tert-butyl 4-(5-(4-(benzo[d]thiazol-2-yloxy)phenyl)-2H-tetrazol-2-yl)-3-((tert-butoxycarbonyl)amino)butanoate | Method A, see above | See above |
| 5b | (R)-tert-butyl 3-((tert-butoxycarbonyl)-amino)-4-(5-(4-((5-chloropyridin-2-yl)-oxy)phenyl)-2H-tetrazol-2-yl)butanoate | Method A | M/z = 531.1 [M + H]$^+$, Rt = 1.39 min (UPLC-MS conditions a). |
| 5c | (R)-tert-butyl 3-((tert-butoxycarbonyl)-amino)-4-(5-(4-((5-chloro-3-fluoropyridin-2-yl)oxy)phenyl)-2H-tetrazol-2-yl)butanoate | Method A | M/z = 549.3 [M + H]$^+$, Rt = 1.37 min (UPLC-MS conditions a). |

-continued

| | Structure and Name | Reaction Parameter | Analytics |
|---|---|---|---|
| 5d | 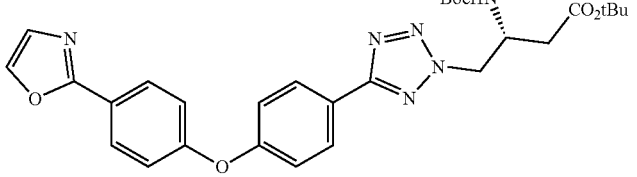<br>(R)-tert-butyl 3-((tert-butoxycarbonyl)-amino)-4-(5-(4-(4-(oxazol-2-yl)phenoxy)-phenyl)-2H-tetrazol-2-yl)butanoate | Method A | M/z = 563.4 [M + H]$^+$, Rt = 1.34 min (UPLC-MS conditions a). |
| 5e | 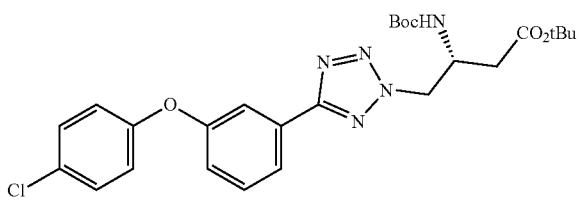 [SMILES: CC(C)(C)OC(=O)C[C@H](Cn1nnc(-c2cccc(Oc3ccc(Cl)cc3)c2)n1)NC(=O)OC(C)(C)C]<br>(R)-tert-butyl 3-((tert-butoxycarbonyl)-amino)-4-(5-(3-(4-chlorophenoxy)-phenyl)-2H-tetrazol-2-yl)butanoate | Method A | M/z = 530.2 [M + H]$^+$, Rt = 1.46 min (UPLC-MS conditions a). |
| 5f | 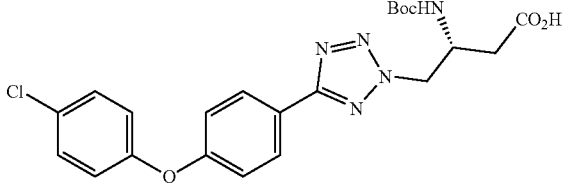 [SMILES: CC(C)(C)OC(=O)N[C@H](CC(=O)O)Cn1nnc(-c2ccc(Oc3ccc(Cl)cc3)cc2)n1]<br>(R)-3-((tert-butoxycarbonyl)amino)-4-(5-(4-(4-chlorophenoxy)phenyl)-2H-tetrazol-2-yl)butanoic acid | Method B, see above | See above |
| 5g | 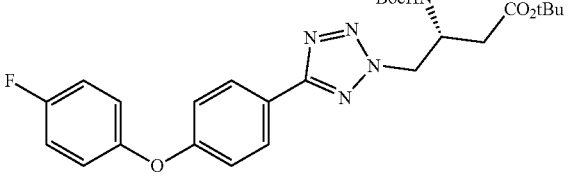<br>(R)-tert-butyl 3-((tert-butoxy-carbonyl)amino)-4-(5-(4-(4-fluorophenoxy)phenyl)-2H-tetrazol-2-yl)butanoate | Method A | M/z = 514.3 [M + H]$^+$, Rt = 1.35 min (UPLC-MS conditions a). |
| 5h | 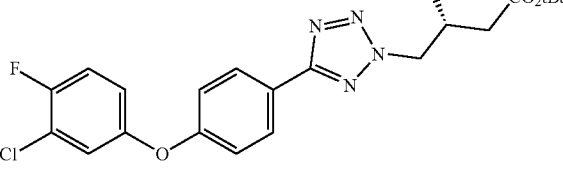<br>(R)-tert-butyl 3-((tert-butoxycarbonyl)amino)-4-(5-(4-(3-chloro-4-fluorophenoxy)phenyl)-2H-tetrazol-2-yl)butanoate | Method A | M/z = 548.3 [M + H]$^+$, Rt = 1.44 min (UPLC-MS conditions a). |

-continued

| | Structure and Name | Reaction Parameter | Analytics |
|---|---|---|---|
| 5i | 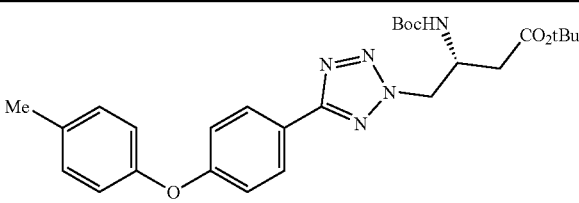<br>(R)-tert-butyl 3-((tert-butoxycarbonyl)-amino)-4-(5-(4-(p-tolyloxy)phenyl)-2H-tetrazol-2-yl)butanoate | Method A | M/z = 510.2 [M + H]$^+$, Rt = 1.43 min (UPLC-MS conditions a). |
| 5j | 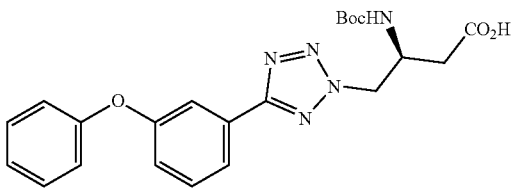 [SMILES: CC(C)(C)OC(=O)N[C@@H](CC(=O)O)Cn1nnc(-c2cccc(Oc3ccccc3)c2)n1]<br>(S)-3-((tert-butoxycarbonyl)amino)-4-(5-(3-phenoxyphenyl)-2H-tetrazol-2-yl)butanoic acid | Method B, using alcohol 1c; flash column chromatography on RP18 silica (0.1% TFA in water:MeCN from 9:1 to 0:1) | M/z = 440.2 [M + H]$^+$, Rt = 1.12 min (UPLC-MS conditions a). |
| 5k | 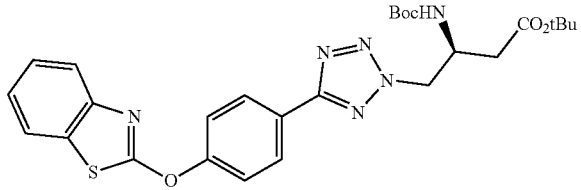 [SMILES: CC(C)(C)OC(=O)C[C@@H](Cn1nnc(-c2ccc(Oc3nc4ccccc4s3)cc2)n1)NC(=O)OC(C)(C)C]<br>(S)-tert-butyl 4-(5-(4-(benzo[d]thiazol-2-yloxy)phenyl)-2H-tetrazol-2-yl)-3-((tert-butoxycarbonyl)amino)butanoate | Method A, using alcohol 1c | M/z = 553.3 [M + H]$^+$, Rt = 6.31 min (UPLC-MS conditions b), $^1$H NMR (400 MHz, DMSO-d$_6$) δ = 8.17 (d, 2H), 7.99 (d, 1H), 7.73 (d, 1H), 7.67 (d, 2H), 7.46 (dd, 1H), 7.38 (dd., 1H), 7.02 (d, 1H), 4.86 (dd, 1H), 4.65 (dd, 1H), 4.27-4.37 (m, 1H), 2.64 (dd, 1H), 2.45 (dd, 1H), 1.40 (s, 9H), 1.26 (s, 9H) ppm. |
| 5l | 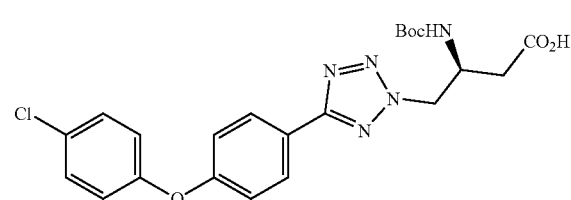<br>(S)-3-((tert-butoxycarbonyl)amino)-4-(5-(4-(4-chlorophenoxy)phenyl)-2H-tetrazol-2-yl)butanoic acid | Method B, using alcohol 1c | M/z = 474.3 [M + H]$^+$, Rt = 5.00 min (UPLC-MS conditions b), Rt = 10.20 min (HPLC conditions c), $^1$H NMR (400 MHz, DMSO-d$_6$) δ = 12.40 (s, br, 1H), 8.06 (d, 2H), 7.49 (d, 2H), 7.19 (d, 2H), 7.14 (d, 2H), 6.97 (d, 1H), 4.80-4.90 (m, 1H), 4.60-4.70 (m, 1H), 4.20-4.35 (m, 1H), 2.55-2.70 (m, 1H), 2.45-2.55 (m, 1H), 1.25 (s, 9H) ppm. |
| 5m | 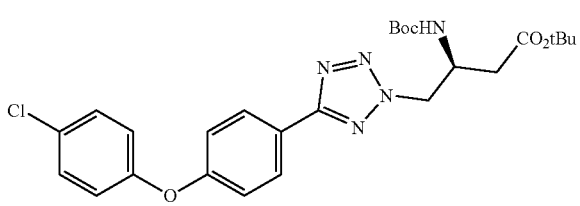 [SMILES: CC(C)(C)OC(=O)C[C@@H](Cn1nnc(-c2ccc(Oc3ccc(Cl)cc3)cc2)n1)NC(=O)OC(C)(C)C]<br>(S)-tert-butyl 3-((tert-butoxy-carbonyl)amino)-4-(5-(4-(4-chlorophenoxy)phenyl)-2H-tetrazol-2-yl)butanoate | Method C, see above | See above |

Synthesis of Substituted Tetrazole Intermediates Via Phenols 6 and 7

(R)-tert-butyl 3-((tert-butoxycarbonyl)amino)-4-(5-(4-hydroxyphenyl)-2H-tetrazol-2-yl)butanoate (6)

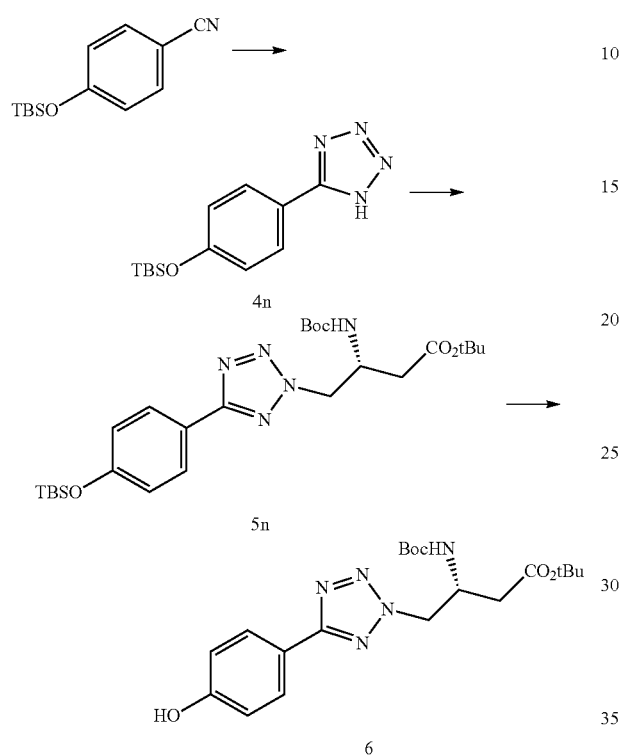

Step A: 5-(4-((tert-butyldimethylsilyl)oxy)phenyl)-1H-tetrazole (4n)

Tetrazole 4n was prepared in analogy to tetrazole 4a and obtained after recrystallization from heptane:EtOAc as a colorless powder.

M/z=277.4 [M+H]$^+$, Rt=1.18 min (UPLC-MS conditions a), $^1$H NMR (400 MHz, DMSO-d$_6$) δ=16.42 (s, br, 1H), 7.71 (d, 2H), 6.83 (d, 2H), 0.73 (s, 9H), 0.00 (s, 6H) ppm.

Step B: (R)-tert-butyl 3-((tert-butoxycarbonyl)-amino)-4-(5-(4-((tert-butyldimethylsilyl)-oxy)phenyl)-2H-tetrazol-2-yl)butanoate (5n)

Alkylated tetrazole 5n was prepared in analogy to Method A.

M/z=534.2 [M+H]$^+$, Rt=1.58 min (UPLC-MS conditions a).

Step C: (R)-tert-butyl 3-((tert-butoxycarbonyl)amino)-4-(5-(4-hydroxyphenyl)-2H-tetrazol-2-yl)butanoate (6)

A solution of (R)-tert-butyl 3-((tert-butoxycarbonyl)-amino)-4-(5-(4-((tert-butyldimethyl-silyl)-oxy)phenyl)-2H-tetrazol-2-yl)butanoate (5n, 2.14 g, 4.00 mmol) in THF (10 mL) was cooled to 0° C., before a solution of TBAF in THF (1 N, 4.40 mL, 4.40 mmol) was added dropwise. After 1 h at that temperature, the reaction mixture was concentrated i. vac. The crude product was purified by flash column chromatography on RP18 silica (0.1% TFA in water:MeCN from 9:1 to 0:1) to afford the title compound 6 as a colorless powder.

M/z=420.4 [M+H]$^+$, Rt=1.07 min (UPLC-MS conditions a), $^1$H NMR (400 MHz, DMSO-d$_6$) δ=9.95 (s, 1H), 7.86 (d, 2H), 6.98 (d, 1H), 6.92 (d, 2H), 4.75 (dd, 1H), 4.59 (dd, 1H), 4.20-4.35 (m, 1H), 2.35-2.65 (m, 2H), 1.39 (s, 9H), 1.25 (s, 9H) ppm.

(R)-tert-butyl 3-((tert-butoxycarbonyl)amino)-4-(5-(3-hydroxyphenyl)-2H-tetrazol-2-yl)butanoate (7)

Step A: 5-(3-((tert-butyldimethylsilyl)oxy)phenyl)-1H-tetrazole (4o)

Tetrazole 4o was prepared in analogy to tetrazole 4a and obtained after flash column chromatography on silica (heptane:EtOAc from 1:0 to 1:1) as a colorless powder.

M/z=277.1 [M+H]$^+$, Rt=1.16 min (UPLC-MS conditions a), $^1$H NMR (400 MHz, CDCl$_3$) δ=7.65 (d, 1H), 7.55-7.59 (m, 1H), 7.41 (t, 1H), 7.03 (dd, 1H), 1.00 (s, 9H), 0.23 (s, 6H) ppm, Tetrazole-NH not detected.

Step B: (R)-tert-butyl 3-((tert-butoxycarbonyl)amino)-4-(5-(3-((tert-butyldimethylsilyl)-oxy)phenyl)-2H-tetrazol-2-yl)butanoate (5o)

Alkylated tetrazole 5o was prepared in analogy to Method A.

M/z=534.3 [M+H]$^+$, Rt=1.55 min (UPLC-MS conditions a).

Step C: (R)-tert-butyl 3-((tert-butoxycarbonyl)amino)-4-(5-(3-hydroxyphenyl)-2H-tetrazol-2-yl)butanoate (7)

Phenol 7 was prepared in analogy to phenol 6 and obtained as a colorless powder.

M/z=420.2 [M+NH$_4$]$^+$, Rt=1.07 min (UPLC-MS conditions a), $^1$H NMR (400 MHz, MeOD-d$_4$) δ=7.52-7.62 (m, 2H), 7.28-7.36 (dd, 1H), 6.90-6.95 (dd, 1H), 4.90 (dd, 1H), 4.75 (dd, 1H), 4.42-4.56 (m, 1H), 2.65 (dd, 1H), 2.52 (dd, 1H), 1.48 (s, 9H), 1.34 (s, 9H) ppm.

Method D: (R)-tert-butyl 3-((tert-butoxycarbonyl)amino)-4-(5-(3-phenethoxyphenyl)-2H-tetrazol-2-yl)butanoate (5p)

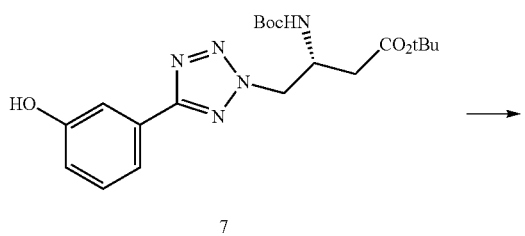

7

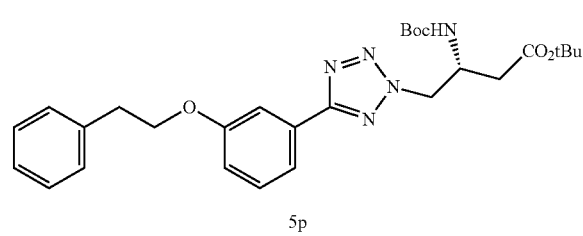

5p

A solution of (R)-tert-butyl 3-((tert-butoxycarbonyl)amino)-4-(5-(3-hydroxyphenyl)-2H-tetrazol-2-yl)butanoate (7, 80 mg, 0.191 mmol), 2-phenylethanol (46 μL, 0.381 mmol) and triphenylphosphine (150 mg, 0.572 mmol) in 2-MeTHF (10 mL) was treated with DIAD (111 μL, 0.572 mmol) and stirred for 4 h at rt. All volatiles were removed i. vac. and the residue was purified by flash column chromatography on RP18 silica (0.1% TFA in water:MeCN from 9:1 to 0:1) to afford ether 5p as a colorless viscous oil.

M/z=524.4 [M+H]$^+$, Rt=1.44 min (UPLC-MS conditions a).

Method E: (R)-tert-butyl 4-(5-(4-(benzyloxy)phenyl)-2H-tetrazol-2-yl)-3-((tert-butoxycarbonyl)amino)butanoate (5r)

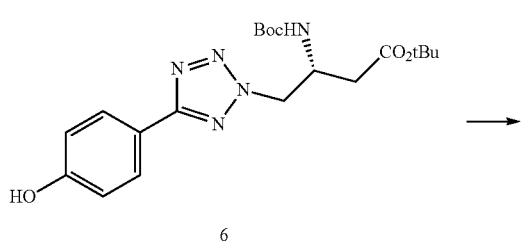

6

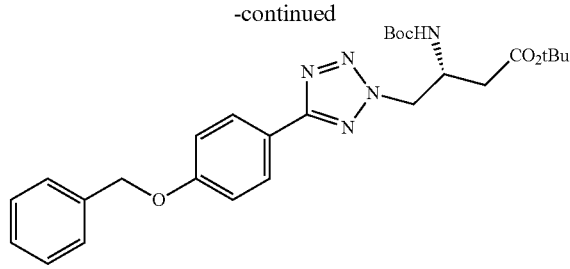

5r

A suspension of (R)-tert-butyl 3-((tert-butoxycarbonyl)amino)-4-(5-(4-hydroxyphenyl)-2H-tetrazol-2-yl)butanoate (6, 90 mg, 0.215 mmol), benzyl bromide (77 μL, 0.644 mmol) and K$_2$CO$_3$ (89 mg, 0.644 mmol) in DMF (0.72 mL) was stirred for 5 h at 65° C. All volatiles were removed i. vac. and the residue was purified by flash column chromatography on RP18 silica (0.1% TFA in water:MeCN from 9:1 to 0:1) to afford ether 5r as a yellowish viscous oil.

M/z=510.2 [M+H]P, Rt=1.35 min (UPLC-MS conditions a).

Method F: (R)-tert-butyl 3-((tert-butoxycarbonyl)amino)-4-(5-(3-((5-(trifluoromethyl)pyridin-2-yl)oxy)phenyl)-2H-tetrazol-2-yl)butanoate (5v)

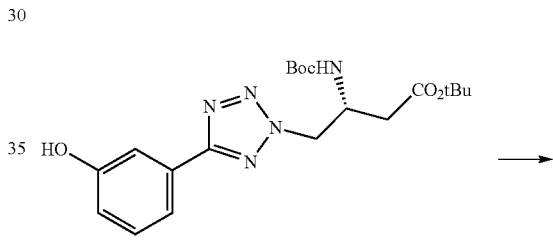

7

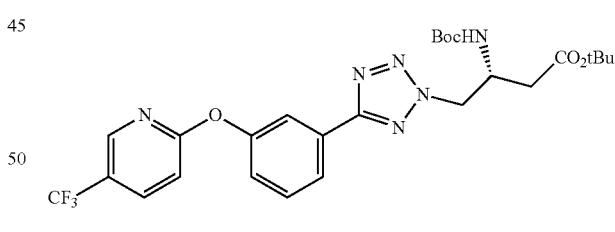

5v

A suspension of (R)-tert-butyl 3-((tert-butoxycarbonyl)amino)-4-(5-(4-hydroxyphenyl)-2H-tetrazol-2-yl)butanoate (7, 100 mg, 0.238 mmol), 2-fluoro-5-(trifluoromethyl)pyridine (88 μL, 0.715 mmol) and K$_2$CO$_3$ (99 mg, 0.715 mmol) in DMF (0.8 mL) was stirred for 5 h at 65° C. All volatiles were removed i. vac. and the residue was purified by flash column chromatography on RP18 silica (0.1% TFA in water:MeCN from 9:1 to 0:1) to afford ether 5v as a yellowish viscous oil.

M/z=565.4 [M+H]$^+$, Rt=1.37 min (UPLC-MS conditions a).

Ethers 5q-y were prepared in analogy to 5p, 5r or 5v

| | Structure and Name | Reaction Parameter | Analytics |
|---|---|---|---|
| 5p | 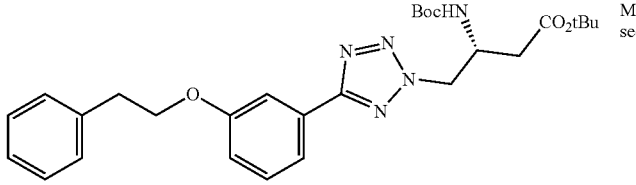<br>(R)-tert-butyl 3-((tert-butoxycarbonyl)-amino)-4-(5-(3-phenethoxyphenyl)-2H-tetrazol-2-yl)butanoate | Method D, see above | See above |
| 5q | 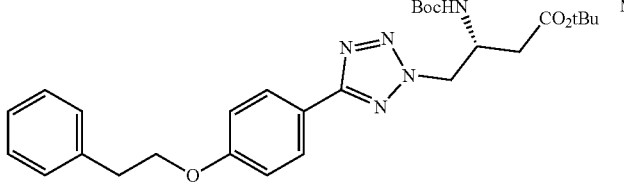<br>(R)-tert-butyl 3-((tert-butoxycarbonyl)-amino)-4-(5-(4-phenethoxyphenyl)-2H-tetrazol-2-yl)butanoate | Method D | M/z = 524.4 [M + H]$^+$, Rt = 1.41 min (UPLC-MS conditions a). |
| 5r | 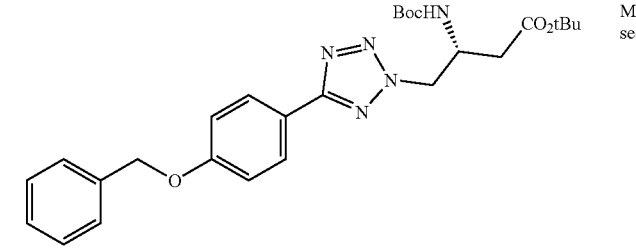<br>(R)-tert-butyl 4-(5-(4-(benzyloxy)phenyl)-2H-tetrazol-2-yl)-3-((tert-butoxycarbonyl)amino)butanoate | Method E, see above | See above |
| 5s | 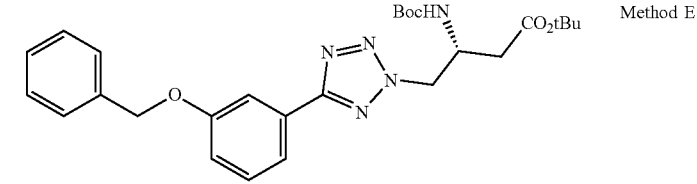<br>(R)-tert-butyl 4-(5-(3-(benzyloxy)phenyl)-2H-tetrazol-2-yl)-3-((tert-butoxycarbonyl)amino)butanoate | Method E | M/z = 510.2 [M + H]$^+$, Rt = 1.37 min (UPLC-MS conditions a). |
| 5t | 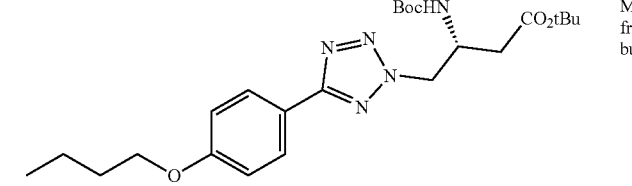<br>(R)-tert-butyl 3-((tert-butoxycarbonyl)-amino)-4-(5-(4-butoxyphenyl)-2H-tetrazol-2-yl)butanoate | Method E, from 6 and butylbromide | M/z = 476.3 [M + H]$^+$, Rt = 1.39 min (UPLC-MS conditions a). |

| | Structure and Name | Reaction Parameter | Analytics |
|---|---|---|---|
| 5u | (R)-tert-butyl 3-((tert-butoxycarbonyl)-amino)-4-(5-(4-(pentyloxy)phenyl)-2H-tetrazol-2-yl)butanoate | Method E, from 6 and pentyl-bromide using $Cs_2CO_3$ | M/z = 490.4 [M + H]$^+$, Rt = 1.49 min (UPLC-MS conditions a). |
| 5v | (R)-tert-butyl 3-((tert-butoxycarbonyl)-amino)-4-(5-(3-((5-(trifluoromethyl)-pyridin-2-yl)oxy)phenyl)-2H-tetrazol-2-yl)butanoate | Method F, see above | See above |
| 5w | (R)-tert-butyl 3-((tert-butoxycarbonyl)-amino)-4-(5-(4-((5-(trifluoromethyl)-pyridin-2-yl)oxy)phenyl)-2H-tetrazol-2-yl)butanoate | Method F, using 2-fluoro-5-(trifluoro-methyl)-pyridine and $Cs_2CO_3$ at 80° C. | M/z = 565.2 [M + H]$^+$, Rt = 1.38 min (UPLC-MS conditions a). |
| 5x | (R)-tert-butyl 4-(5-(3-(benzo[d]thiazol-2-yloxy)phenyl)-2H-tetrazol-2-yl)-3-((tert-butoxycarbonyl)amino)butanoate | Method F, 22 h at 80° C. | M/z = 553.4 [M + H]$^+$, Rt = 1.41 min (UPLC-MS conditions a). |
| 5y | (R)-tert-butyl 3-((tert-butoxycarbonyl)-amino)-4-(5-(3-(3,5-difluorophenoxy)-phenyl)-2H-tetrazol-2-yl)butanoate | Method F, using 1,3,5-trifluoro-benzene (8 eq.), $Cs_2CO_3$ 22 h at 70° C. | M/z = 532.3 [M + H]$^+$, Rt = 1.41 min (UPLC-MS conditions a). |

| | Structure and Name | Reaction Parameter | Analytics |
|---|---|---|---|
| 5z | (S)-tert-butyl 3-((tert-butoxycarbonyl)-amino)-4-(5-(4-(p-tolyloxy)phenyl)-2H-tetrazol-2-yl)butanoate | MethodC, 4 h, rt | M/z = 510.3 [M + H]$^+$, Rt = 1.42 min (UPLC-MS conditions a), $^1$H NMR (400 MHz, DMSO-d$_6$) δ = 8.02 (d, 2H), 7.26 (d, 2H), 7.10 (d, 2H), 7.01 (d, 2H), 6.98 (s, 1H), 4.81 (dd, 1H), 4.61 (dd, 1H), 4.25-4.35 (m, 1H), 2.60 (dd, 1H), 2.43 (dd, 1H), 2.32 (s, 3H), 1.39 (s, 9H), 1.24 (s, 9H) ppm. |

Example 1

Method G: (R)-3-amino-4-(5-(4-(benzo[d]thiazol-2-yloxy)phenyl)-2H-tetrazol-2-yl)butanoic acid

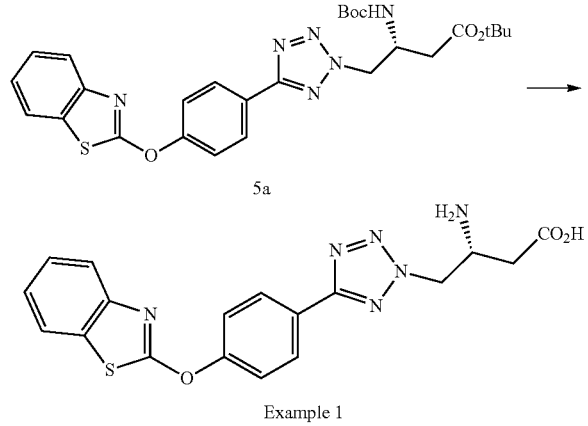

A solution of (R)-tert-butyl 4-(5-(4-(benzo[d]thiazol-2-yloxy)phenyl)-2H-tetrazol-2-yl)-3-((tert-butoxycarbonyl)amino)butanoate (5a, 414 mg, 0.749 mmol) in 4 N HCl in dioxane (1.87 mL, 7.49 mmol) was heated to 40° C. for 3 h. The resulting suspension was filtered, and the crude product was washed with acetone affording the hydrochloride of the desired product (Example 1) as a colorless solid.

M/z=397.0 [M+H]$^+$, Rt=2.61 min (UPLC-MS conditions b), Rt=8.80 min (HPLC conditions e), $^1$H NMR (400 MHz, MeOD-d$_4$) δ=8.31 (d, 2H), 7.83 (d, 1H), 7.68 (d, 1H), 7.60 (d, 2H), 7.45 (dd, 1H), 7.35 (dd, 1H), 5.16 (d, 2H), 4.29 (quint, 1H), 2.95 (d, 1H), 2.79 (dd, 1H) ppm.

Examples (Ex.) 2-23 were Prepared in Analogy to Example 1 (Method G) and Obtained as Hydrochloride Salts

| Ex. | Structure and Name | Reaction Parameter | Analytics |
|---|---|---|---|
| 1 | (R)-3-amino-4-(5-(4-(benzo[d]thiazol-2-yloxy)phenyl)-2H-tetrazol-2-yl)butanoic acid | See above | See above |
| 2 | (R)-3-amino-4-(5-(4-((5-chloropyridin-2-yl)oxy)phenyl)-2H-tetrazol-2-yl)butanoic acid | | M/z = 375.0 [M + H]$^+$, Rt = 2.21 min (UPLC-MS conditions b), $^1$H NMR (400 MHz, DMSO-d$_6$) δ = 12.8 (s, br, 1H), 8.44 (s, br, 3H), 8.25 (d, 1H), 8.13 (d, 2H), 8.02 (dd, 1H), 7.36 (d, 2H), 7.20 (d, 1H), 5.08 (d, 2H), 4.00-4.28 (m, 1H), 2.81 (d, 2H) ppm. |

| Ex. | Structure and Name | Reaction Parameter | Analytics |
|---|---|---|---|
| 3 | 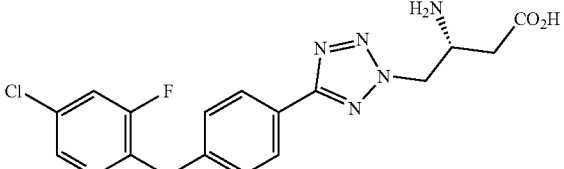<br>(R)-3-amino-4-(5-(4-((5-chloro-3-fluoropyridin-2-yl)oxy)phenyl)-2H-tetrazol-2-yl)butanoic acid | Flash column chromatography on RP18 silica (0.1% TFA in water:MeCN from 9:1 to 0:1); Then TFA/HCl salt exchange | M/z = 393.2 [M + H]$^+$, Rt = 2.44 min (UPLC-MS conditions b), $^1$H NMR (400 MHz, DMSO-d$_6$) δ = 12.7 (s, br, 1H), 8.5 (s, br, 3H), 8.29 (dd, 1H), 8.15 (d, 2H), 8.11 (d, 1H), 7.43 (d, 2H), 5.09 (d, 2H), 4.09 (quint, 1H), 2.81 (d, 2H) ppm, $^{19}$F NMR (376 MHz, DMSO-d$_6$) δ = −134.00 (d, 1F) ppm. |
| 4 | 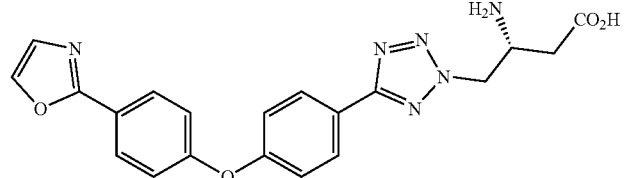<br>(R)-3-amino-4-(5-(4-(4-(oxazol-2-yl)-phenoxy)phenyl)-2H-tetrazol-2-yl)-butanoic acid | | M/z = 407.3 [M + H]$^+$, Rt = 2.50 min (UPLC-MS conditions b), $^1$H NMR (400 MHz, MeOD-d$_4$) δ = 8.23 (d, 2H), 8.08 (d, 2H), 8.03 (s, 1H), 7.36 (s, 1H), 7.19-7.25 (m, 4H), 5.14 (d, 2H), 4.27 (quint, 1H), 2.95 (dd, 1H), 2.78 (dd, 1H) ppm. |
| 5 | 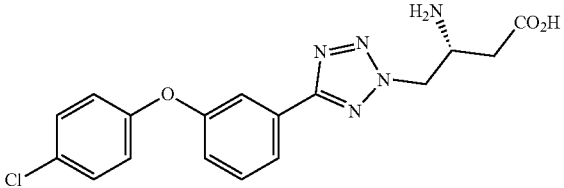 [SMILES: N[C@H](CC(=O)O)Cn1nnc(-c2cccc(Oc3ccc(Cl)cc3)c2)n1]<br>(R)-3-amino-4-(5-(3-(4-chlorophenoxy)phenyl)-2H-tetrazol-2-yl)butanoic acid | | M/z = 407.3 [M + H]$^+$, Rt = 2.50 min (UPLC-MS conditions b), $^1$H NMR (400 MHz, MeOD-d$_4$) δ = 8.23 (d, 2H), 8.08 (d, 2H), 8.03 (s, 1H), 7.36 (s, 1H), 7.19-7.25 (m, 4H), 5.14 (d, 2H), 4.27 (quint, 1H), 2.95 (dd, 1H), 2.78 (dd, 1H) ppm. |
| 6 | 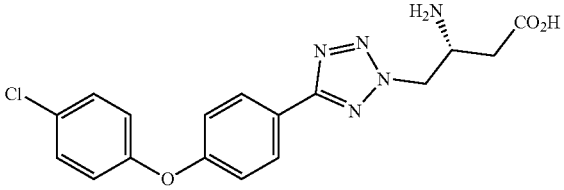 [SMILES: N[C@H](CC(=O)O)Cn1nnc(-c2ccc(Oc3ccc(Cl)cc3)cc2)n1]<br>(R)-3-amino-4-(5-(4-(4-chlorophenoxy)-phenyl)-2H-tetrazol-2-yl)butanoic acid | From carboxylic acid 5f: rt, 4 h | M/z = 374.2 [M + H]$^+$, Rt = 2.87 min (UPLC-MS conditions b), Rt = 8.84 min (HPLC conditions d), $^1$H NMR (400 MHz, MeOD-d$_4$) δ = 8.16 (d, 2H), 7.41 (d, 2H), 7.14 (d, 2H), 7.07 (d, 2H), 5.13 (d, 2H), 4.26 (quint, 1H), 2.92 (dd, 1H), 2.76 (dd, 1H) ppm. |
| 7 | 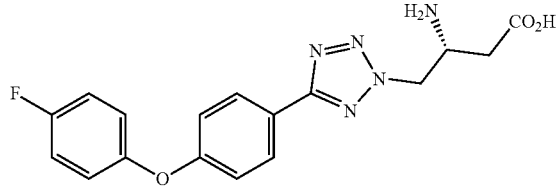 [SMILES: N[C@H](CC(=O)O)Cn1nnc(-c2ccc(Oc3ccc(F)cc3)cc2)n1]<br>(R)-3-amino-4-(5-(4-(4-fluorophenoxy)-phenyl)-2H-tetrazol-2-yl)butanoic acid | rt, 64 h | M/z = 358.2 [M + H]$^+$, Rt = 2.48 min (UPLC-MS conditions b), $^1$H NMR (400 MHz, MeOD-d$_4$) δ = 8.15 (d, 2H), 7.10-7.20 (m, 6H), 5.14 (d, 2H), 4.28 (quint, 1H), 2.95 (dd, 1H), 2.78 (d, 1H) ppm. |

| Ex. | Structure and Name | Reaction Parameter | Analytics |
|---|---|---|---|
| 8 | 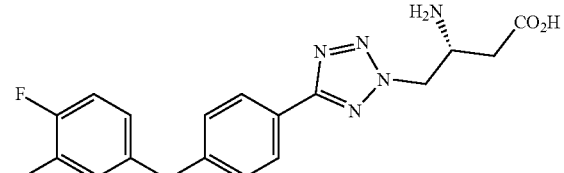<br>(R)-3-amino-4-(5-(4-(3-chloro-4-fluorophenoxy)phenyl)-2H-tetrazol-2-yl)butanoic acid | Reaction mixture concentrated i. vac. | M/z = 392.3 [M + H]$^+$, Rt = 3.02 min (UPLC-MS conditions b), $^1$H NMR (400 MHz, MeOD-d$_4$) δ = 8.20 (d, 2H), 7.29-7.38 (m, 1H), 7.24 (d, 1H), 7.17 (d, 2H), 7.04-7.11 (m, 1H), 5.15 (d, 2H), 4.22-4.33 (m, 1H), 2.93 (d, 1H), 2.81 (d, 1H) ppm. |
| 9 | 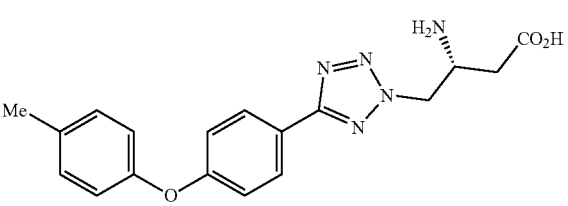 [SMILES: Cc1ccc(Oc2ccc(-c3nnn(C[C@H](N)CC(=O)O)n3)cc2)cc1]<br>(R)-3-amino-4-(5-(4-(p-tolyloxy)phenyl)-2H-tetrazol-2-yl)butanoic acid | rt, 64 h | M/z = 354.2 [M + H]$^+$, Rt = 2.82 min (UPLC-MS conditions b), $^1$H NMR (400 MHz, MeOD-d$_4$) δ = 8.13 (d, 2H), 7.25 (d, 2H), 7.09 (d, 2H), 6.99 (d, 2H), 5.13 (d, 2H), 4.28 (quint, 1H), 2.95 (dd, 1H), 2.78 (dd, 1H), 2.37 (s, 3H) ppm. |
| 10 | 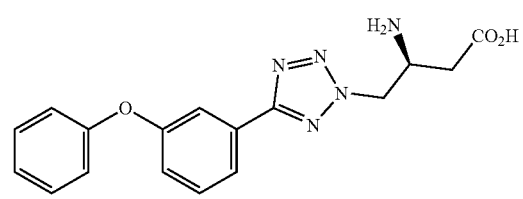 [SMILES: N[C@@H](CC(=O)O)Cn1nnc(-c2cccc(Oc3ccccc3)c2)n1]<br>(S)-3-amino-4-(5-(3-phenoxyphenyl)-2H-tetrazol-2-yl)butanoic acid | From carboxylic acid 5j: flash column chromatography on RP18 silica (0.1% TFA in water:MeCN from 9:1 to 0:1); Then TFA/HCl salt exchange | M/z = 340.2 [M + H]$^+$, Rt = 2.43 min (UPLC-MS conditions b), $^1$H NMR (400 MHz, MeOD-d$_4$) δ = 7.91 (d, 1H), 7.70-7.75 (m, 1H), 7.53 (t, 1H), 7.36-7.44 (m, 2H), 7.12-7.22 (m, 2H), 7.06 (d, 2H), 5.12 (d, 2H), 4.24 (quint, 1H), 2.92 (d, 1H), 2.75 (d, 1H) ppm. |
| 11 | 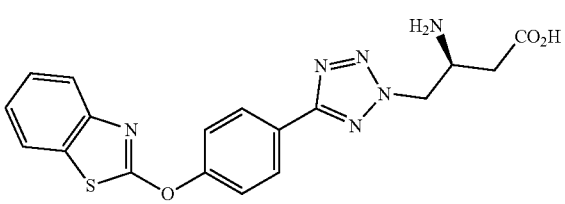 [SMILES: N[C@@H](CC(=O)O)Cn1nnc(-c2ccc(Oc3nc4ccccc4s3)cc2)n1]<br>(S)-3-amino-4-(5-(4-(benzo[d]thiazol-2-yloxy)phenyl)-2H-tetrazol-2-yl)butanoic acid | Washed with dioxane, acetone and pentane | M/z = 397.2 [M + H]$^+$, Rt = 2.66 min (UPLC-MS conditions b), Rt = 17.45 min (HPLC conditions e), $^1$H NMR (400 MHz, MeOD-d$_4$) δ = 8.34 (d, 2H), 7.85 (d, 1H), 7.71 (d, 1H), 7.62 (d, 2H), 7.47 (t, 1H), 7.37 (t, 1H), 5.19 (d, 2H), 4.29 (quint, 1H), 2.98 (dd, 1H), 2.81 (dd, 1H) ppm. |
| 12 | 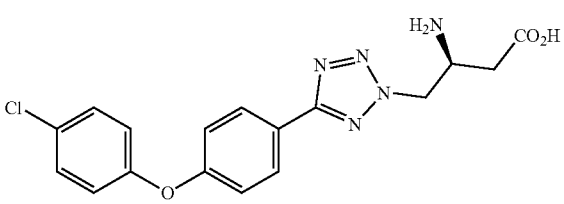 [SMILES: N[C@@H](CC(=O)O)Cn1nnc(-c2ccc(Oc3ccc(Cl)cc3)cc2)n1]<br>(S)-3-amino-4-(5-(4-(4-chlorophenoxy)-phenyl)-2H-tetrazol-2-yl)butanoic acid | From carboxylic acid 5l: rt, 4 h; or from ester 5m: 40° C., 3 h | M/z = 374.2 [M + H]$^+$, Rt = 2.97 min (UPLC-MS conditions b), Rt = 10.67 min (HPLC conditions d), $^1$H NMR (400 MHz, MeOD-d$_4$) δ = 8.16 (d, 2H), 7.41 (d, 2H), 7.14 (d, 2H), 7.07 (d, 2H), 5.13 (d, 2H), 4.20-4.31 (m, 1H), 2.92 (dd, 1H), 2.76 (dd, 1H) ppm. |

-continued

| Ex. | Structure and Name | Reaction Parameter | Analytics |
|---|---|---|---|
| 13 | 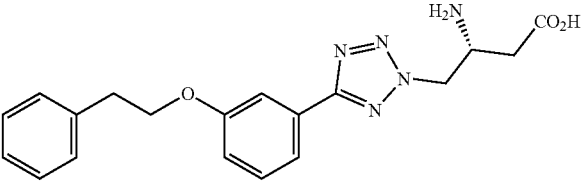 [SMILES: N[C@H](CC(=O)O)Cn1nnc(-c2cccc(OCCc3ccccc3)c2)n1]<br>(R)-3-amino-4-(5-(3-phenethoxyphenyl)-2H-tetrazol-2-yl)butanoic acid | Evaporated to dryness, then triturated with acetone and heptane | M/z = 368.2 $[M + H]^+$, Rt = 2.84 min (UPLC-MS conditions b), $^1$H NMR (400 MHz, MeOD-$d_4$) δ = 7.73 (d, 1H), 7.68 (m, 1H), 7.43 (t, 1H), 7.27-7.36 (m, 4H), 7.18-7.23 (m, 1H), 7.08 (d, 1H), 5.13 (d, 2H), 4.20-4.32 (m, 3H), 3.12 (t, 2H), 2.92 (dd, 1H), 2.74 (dd, 1H) ppm. |
| 14 | 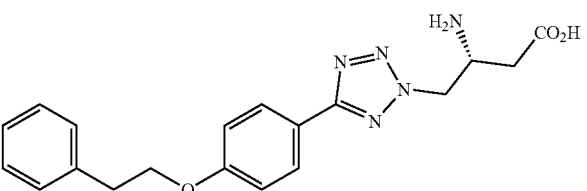<br>(R)-3-amino-4-(5-(4-phenethoxyphenyl)-2H-tetrazol-2-yl)butanoic acid | Evaporated to dryness, then triturated with acetone and heptane | M/z = 368.2 $[M + H]^+$, Rt = 2.75 min (UPLC-MS conditions b), $^1$H NMR (400 MHz, MeOD-$d_4$) δ = 8.07 (d, 2H), 7.27-7.35 (m, 4H), 7.17-7.23 (m, 1H), 7.07 (d, 2H), 5.10 (d, 2H), 4.18-4.32 (m, 3H), 3.11 (t, 2H), 2.92 (dd, 1H), 2.75 (dd, 1H) ppm. |
| 15 | 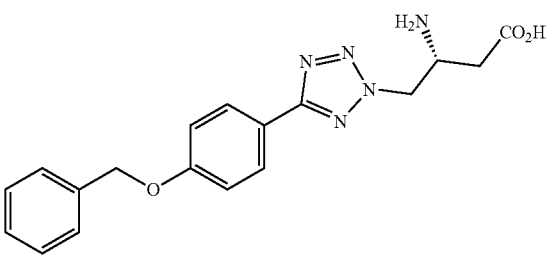 [SMILES: N[C@H](CC(=O)O)Cn1nnc(-c2ccc(OCc3ccccc3)cc2)n1]<br>(R)-3-amino-4-(5-(4-(benzyloxy)phenyl)-2H-tetrazol-2-yl)butanoic acid | Washed with dioxane | M/z = 354.2 $[M + H]^+$, Rt = 2.51 min (UPLC-MS conditions b), $^1$H NMR (400 MHz, MeOD-$d_4$) δ = 8.09 (d, 2H), 7.46 (d, 2H), 7.39 (t, 2H), 7.29-7.36 (m, 1H), 7.16 (d, 2H), 5.18 (s, 2H), 5.10 (d, 2H), 4.20-4.30 (m, 1H), 2.93 (dd, 1H), 2.75 (dd, 1H) ppm. |
| 16 | 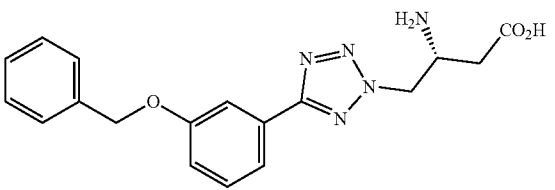 [SMILES: N[C@H](CC(=O)O)Cn1nnc(-c2cccc(OCc3ccccc3)c2)n1]<br>(R)-3-amino-4-(5-(3-(benzyloxy)phenyl)-2H-tetrazol-2-yl)butanoic acid | Washed with dioxane | M/z = 354.3 $[M + H]^+$, Rt = 2.50 min (UPLC-MS conditions b), $^1$H NMR (400 MHz, MeOD-$d_4$) δ = 7.79-7.81 (m, 1H), 7.77 (d, 1H), 7.44-7.52 (m, 3H), 7.38-7.43 (m, 2H), 7.31-7.36 (m, 1H), 7.20 (dd, 1H), 5.20 (s, 2H), 5.16 (d, 2H), 4.24-4.32 (m, 1H), 2.96 (dd, 1H), 2.78 (dd, 1H) ppm. |
| 17 | 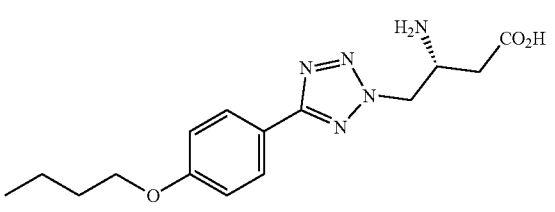 [SMILES: CCCCOc1ccc(-c2nnn(C[C@H](N)CC(=O)O)n2)cc1]<br>(R)-3-amino-4-(5-(4-butoxyphenyl)-2H-tetrazol-2-yl)butanoic acid | Evaporated to dryness, then triturated with acetone and heptane | M/z = 320.2 $[M + H]^+$, Rt = 2.43 min (UPLC-MS conditions b), $^1$H NMR (400 MHz, MeOD-$d_4$) δ = 8.07 (d, 2H), 7.06 (d, 2H), 5.10 (d, 2H), 4.20-4.30 (m, 1H), 4.06 (t, 2H), 2.91 (dd, 1H), 2.75 (dd, 1H), 1.75-1.85 (m, 2H), 1.48-1.60 (m, 2H), 1.01 (t, 3H) ppm. |

-continued

| Ex. | Structure and Name | Reaction Parameter | Analytics |
|---|---|---|---|
| 18 | 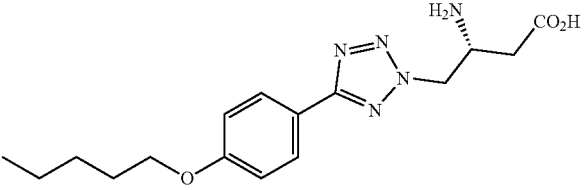 [SMILES: CCCCCOc1ccc(-c2nnn(C[C@H](N)CC(=O)O)n2)cc1]<br>(R)-3-amino-4-(5-(4-(pentyloxy)phenyl)-2H-tetrazol-2-yl)butanoic acid | Flash column chromatography on RP18 silica (0.1% TFA in water:MeCN from 9:1 to 0:1); Then TFA/HCl salt exchange | M/z = 334.2 [M + H]$^+$, Rt = 2.99 min (UPLC-MS conditions b), $^1$H NMR (400 MHz, DMSO-d$_6$) δ = 8.6 (s, br, 3H), 8.00 (d, 2H), 7.12 (d, 2H), 5.04 (d, 2H), 4.02-4.12 (m, 3H), 2.79 (d, 2H), 1.70-1.80 (m, 2H), 1.29-1.49 (m, 4H), 0.91 (t, 3H) ppm. |
| 19 | 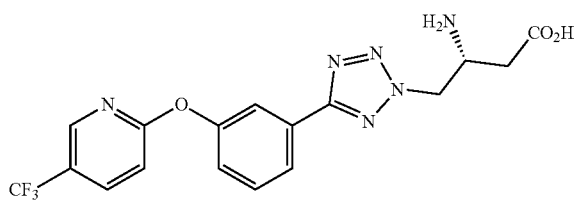 [SMILES: N[C@H](CC(=O)O)Cn1nnc(-c2cccc(Oc3ccc(C(F)(F)F)cn3)c2)n1]<br>(R)-3-amino-4-(5-(3-((5-(trifluoro-methyl)pyridin-2-yl)oxy)phenyl)-2H-tetrazol-2-yl)butanoic acid | Evaporated to dryness, then triturated with acetone and heptane | M/z = 409.3 [M + H]$^+$, Rt = 2.50 min (UPLC-MS conditions b), $^1$H NMR (400 MHz, MeOD-d$_4$) δ = 8.44 (d, 1H), 8.14 (dd, 1H), 8.08 (dd, 1H), 7.93-7.97 (m, 1H), 7.63 (t, 1H), 7.35 (dd, 1H), 7.24 (d, 1H), 5.14 (d, 2H), 4.23-4.29 (m, 1H), 2.92 (dd, 1H), 2.75 (dd, 1H) ppm. |
| 20 | 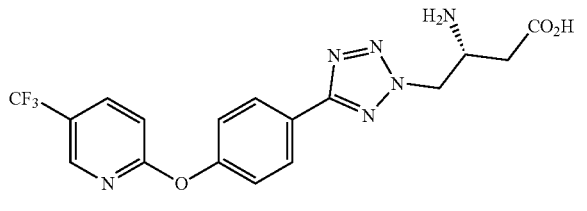 [SMILES: N[C@H](CC(=O)O)Cn1nnc(-c2ccc(Oc3ccc(C(F)(F)F)cn3)cc2)n1]<br>(R)-3-amino-4-(5-(4-((5-(trifluoro-methyl)pyridin-2-yl)oxy)phenyl)-2H-tetrazol-2-yl)butanoic acid | Flash column chromatography on RP18 silica (0.1% TFA in water:MeCN from 9:1 to 0:1); Then TFA/HCl salt exchange | M/z = 409.1 [M + H]$^+$, Rt = 2.59 min (UPLC-MS conditions b), $^1$H NMR (400 MHz, MeOD-d$_4$) δ = 8.46 (s, 1H), 8.25 (d, 2H), 8.14 (dd, 1 H), 7.36 (d, 2H), 7.23 (d, 1H), 5.15 (d, 2H), 4.22-4.33 (m, 1H), 2.94 (dd, 1H), 2.77 (dd, 1H) ppm. |
| 21 | 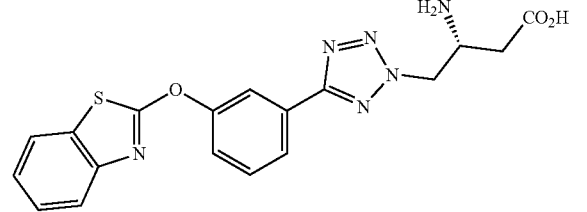 [SMILES: N[C@H](CC(=O)O)Cn1nnc(-c2cccc(Oc3nc4ccccc4s3)c2)n1]<br>(R)-3-amino-4-(5-(3-(benzo[d]thiazol-2-yloxy)phenyl)-2H-tetrazol-2-yl)butanoic acid | Evaporated to dryness, then triturated with acetone and heptane | M/z = 397.2 [M + H]$^+$, Rt = 2.62 min (UPLC-MS conditions b), $^1$H NMR (400 MHz, MeOD-d$_4$) δ = 8.15-8.23 (m, 2H), 7.85 (d, 1H), 7.67-7.74 (m, 2H), 7.57-7.65 (m, 1H), 7.46 (t, 1H), 7.34-7.38 (m, 1H), 5.17 (d, 2H), 4.24-4.33 (m, 1H), 2.94 (dd, 1H), 2.78 (dd, 1H) ppm. |
| 22 | 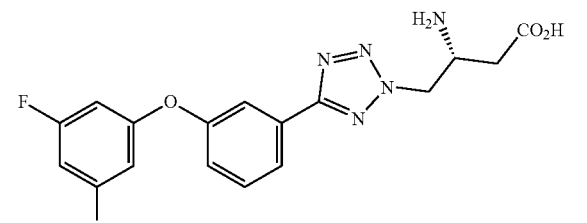<br>(R)-3-amino-4-(5-(3-(3,5-difluoro-phenoxy)phenyl)-2H-tetrazol-2-yl)butanoic acid | Evaporated to dryness, then triturated with acetone and heptane | M/z = 376.3 [M + H]$^+$, Rt = 2.69 min (UPLC-MS conditions b), $^1$H NMR (400 MHz, MeOD-d$_4$) δ = 8.05 (d, 1H), 7.84-7.87 (m, 1H), 7.64 (t, 1H), 7.26-7.33 (m, 1H), 6.76 (tt, 1H), 6.65 (dd, 2H), 5.15 (d, 2H), 4.23-4.33 (m, 1H), 2.93 (dd, 1H), 2.77 (dd, 1H) ppm. |

| Ex. | Structure and Name | Reaction Parameter | Analytics |
|---|---|---|---|
| 23 | 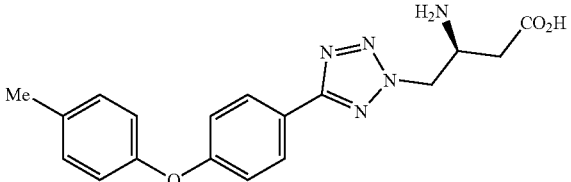(S)-3-amino-4-(5-(4-(p-tolyloxy)phenyl)-2H-tetrazol-2-yl)butanoic acid | Washed with dioxane, acetone and pentane | M/z = 354.2 [M + H]+, Rt = 2.74 min (UPLC-MS conditions b), 1H NMR (400 MHz, MeOD-d4) δ = 8.13 (d, 2H), 7.25 (d, 2H), 7.09 (d, 2H), 6.99 (d, 2H), 5.14 (d, 2H), 4.24-4.31 (m, 1H), 2.95 (dd, 1H), 2.78 (dd, 1H), 2.37 (s, 3H) ppm. |

Example 24

(R)-3-amino-4-(5-(4-(4-fluorophenoxy) phenyl)-1,3,4-oxadiazol-2-yl)butanoic acid

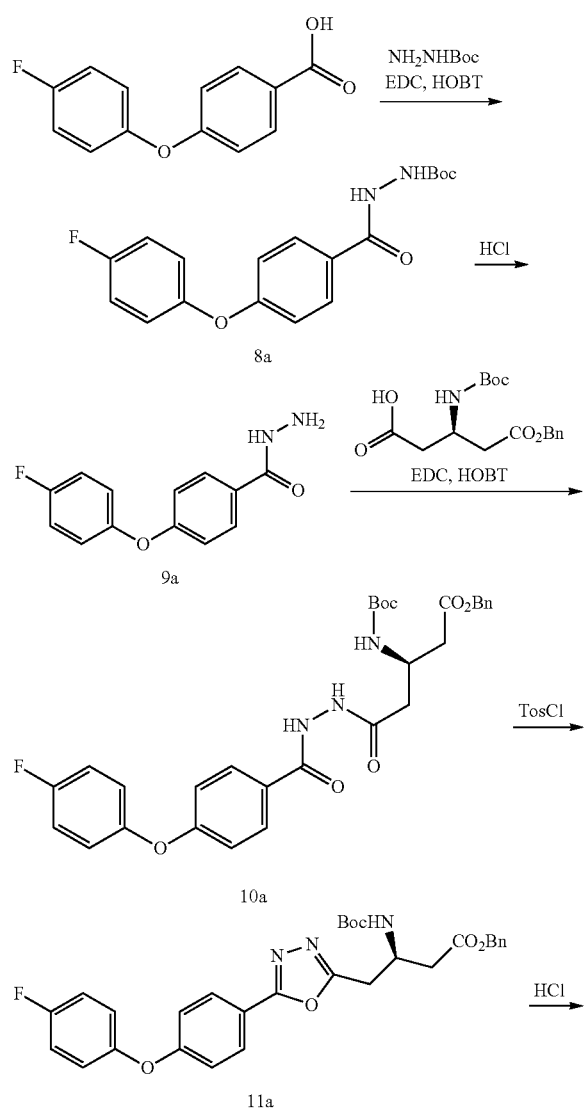

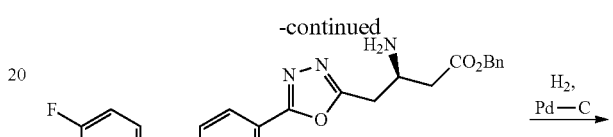

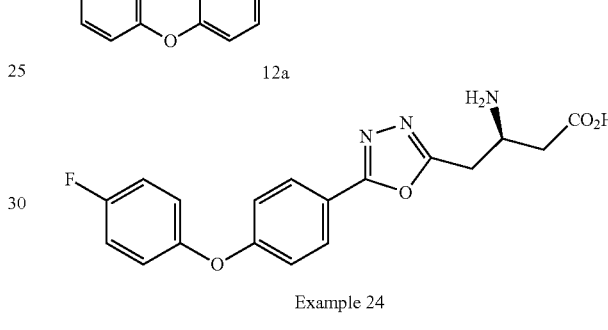

Example 24

Step A: tert-butyl 2-(4-(4-fluorophenoxy)benzoyl)hydrazinecarboxylate (8a)

4-(4-fluorophenoxy)benzoic acid (5.5 g, 23.69 mmol), tert-butyl hydrazinecarboxylate (3.13 g, 23.7 mmol), HOBT (5.44 g, 35.5 mmol), Et3N (4.92 mL, 35.5 mmol) and EDC×HCl (6.81 g, 35.5 mmol) were dissolved in DCM (90 mL). The brown reaction mixture was stirred for 5 h at rt. The reaction mixture was concentrated i. vac. and partitioned between water (15 mL) and DCM (35 mL). The aqueous layer was extracted with DCM (2×30 mL) and the combined organic layers were dried over Na2SO4 and concentrated i. vac. The crude product was purified by flash column chromatography on silica (0-100% EtOAc in cyclohexane). The purified product was triturated with diethylether and obtained as a colorless solid.

M/z=345.2 [M−H]+, Rt=1.03 min (UPLC-MS conditions a), 1H NMR (400 MHz, DMSO-d6) δ=10.13 (br s, 1H), 8.88 (br s, 1H), 7.88 (d, 2H), 7.30 (dd, 2H), 7.15-7.20 (m, 2H), 7.02 (d, 2H), 1.43 (s, 9H) ppm.

Step B: 4-(4-fluorophenoxy)benzohydrazide (9a)

HCl in dioxane (4 N, 30.3 mL, 121 mmol) was added to tert-butyl 2-(4-(4-fluorophenoxy)-benzoyl)hydrazinecarboxylate (8a, 2.80 g, 8.08 mmol) and stirred for 1.5 h at rt. The reaction mixture was evaporated i. vac. and the residue was triturated with TBME to afford a pale yellow solid.

M/z=247.1 [M+H]+, Rt=0.78 min (UPLC-MS conditions a), $^1$H NMR (400 MHz, DMSO-$d_6$) δ=11.55 (br s, 1H), 10.43 (br s, 2H), 7.96 (d, 2H), 7.32 (dd, 2H), 7.2 (m, 2H), 7.07 (d, 2H) ppm.

Step C: (R)-benzyl 3-((tert-butoxycarbonyl)amino)-5-(2-(4-(4-fluorophenoxy)benzoyl) hydrazinyl)-5-oxopentanoate (10a)

4-(4-fluorophenoxy)benzohydrazide (9a, 1.51 g, 4.74 mmol), (R)-5-(benzyloxy)-3-((tert-butoxycarbonyl)amino)-5-oxopentanoic acid (1.6 g, 4.74 mmol), HOBT (0.944 g, 6.17 mmol), Et$_3$N (1.32 mL, 9.49 mmol) and EDC×HCl (1.36 g, 7.11 mmol) were dissolved in DCM (18 mL). The brown reaction mixture was stirred for 16 h at rt. Then the reaction mixture was diluted with water (15 mL) and the aqueous layer was extracted with DCM (2×30 mL). The combined organic layers were dried over Na$_2$SO$_4$ and evaporated under reduced pressure. The crude product was purified by flash column chromatography on silica (0-70% EtOAc in cyclohexane) to give a colorless solid.

M/z=566.2 [M+H]+, Rt=1.16 min (UPLC-MS conditions a), $^1$H NMR (400 MHz, DMSO-$d_6$) δ=10.27 (br s, 1H), 9.93 (br s, 1H), 7.89 (d, 2H), 7.25-7.40 (m, 7H), 7.19 (m, 2H), 7.04 (m, 2H), 5.08 (d, 2H), 4.21 (br m, 1H), 2.70-2.75 (dd, 1H), 2.37-2.55 (m, 3H), 1.38 (s, 9H) ppm.

Step D: (R)-benzyl 3-((tert-butoxycarbonyl) amino)-4-(5-(4-(4-fluorophenoxy) phenyl)-1,3,4-oxadiazol-2-yl)butanoate (11a)

(R)-benzyl 3-((tert-butoxycarbonyl)amino)-5-(2-(4-(4-fluorophenoxy)benzoyl) hydrazinyl)-5-oxopentanoate (10a, 2.10 g, 3.71 mmol) and TosCl (0.779 g, 4.08 mmol) were dissolved in DCM (35 mL), then Et$_3$N (0.772 mL, 5.57 mmol) was added within 2 min. The reaction mixture was allowed to stir for 16 h at rt. Then the reaction mixture was quenched with water and extracted three times with DCM. The combined organic layers were washed with brine, dried over Na$_2$SO$_4$, filtered and evaporated. The crude product was purified by flash column chromatography on silica (0-50% EtOAc in cyclohexane) to yield 11a as a colorless foam.

M/z=548.2 [M+H]+, Rt=1.33 min (UPLC-MS conditions a), $^1$H NMR (400 MHz, DMSO-$d_6$) δ=7.94 (d, 2H), 7.25-7.40 (m, 6H), 7.15-7.25 (m, 2H), 7.14 (d, 2H), 7.05 (m, 1H), 5.09 (s, 2H), 4.28 (br m, 1H), 3.17 (dd, 1H), 3.01 (dd, 1H), 2.75 (dd, 1H), 2.70 (dd, 1H), 1.28 (s, 9H) ppm.

Step E: (R)-benzyl 3-amino-4-(5-(4-(4-fluoro-phenoxy)phenyl)-1,3,4-oxadiazol-2-yl)butanoate (12a)

(R)-benzyl 3-((tert-butoxycarbonyl) amino)-4-(5-(4-(4-fluorophenoxy) phenyl)-1,3,4-oxadiazol-2-yl)butanoate (11a, 1.50 g, 2.74 mmol) was dissolved in 4 N HCl in dioxane (13.7 mL, 54.8 mmol) and stirred for 1.5 h at rt. Then the reaction mixture was evaporated under reduced pressure. The residue was triturated with diethylether affording the title compound 12a as a colorless solid which was used in the next step without further purification.

M/z=448.3 [M+H]+, Rt=0.95 min (UPLC-MS conditions a), $^1$H NMR (400 MHz, DMSO-$d_6$) δ=8.43 (br s, 2H), 7.98 (d, 2H), 7.30-7.40 (m, 7H), 7.20-7.25 (m, 2H), 7.13-7.15 (m, 2H), 5.12 (s, 2H), 4.00 (m, 1H), 3.57 (d, 1H), 3.40 (d, 1H), 2.96 (d, 1H) ppm.

Step F: (R)-3-amino-4-(5-(4-(4-fluorophenoxy) phenyl)-1,3,4-oxadiazol-2-yl)butanoic acid (Example 24)

(R)-benzyl 3-amino-4-(5-(4-(4-fluoro-phenoxy)phenyl)-1,3,4-oxadiazol-2-yl)butanoate (12a, 200 mg, 0.447 mmol) was dissolved in methanol (5 mL) and added to a flask containing 10% Pd/C (47.6 mg, 0.045 mmol) under Argon. The mixture was degassed and flushed three times with hydrogen. The reaction mixture was stirred under an atmosphere of hydrogen for 3 h at rt. The reaction mixture was filtered over a plug of celite and evaporated under reduced pressure. No further purification was needed.

M/z=358.2 [M+H]+, Rt=0.71 min (UPLC-MS conditions a), $^1$H NMR (400 MHz, DMSO-$d_6$) δ=8.00 (d, 2H), 7.26-7.35 (m, 2H), 7.03-7.26 (m, 4H), 4.11 (m, 1H), 3.8 (m, 1H), 3.17 (m, 1H), 2.79 (d, 2H) ppm.

Example 25

(R)-3-amino-4-(5-(4-(4-chlorophenoxy) phenyl)-1,3,4-oxadiazol-2-yl)butanoic acid

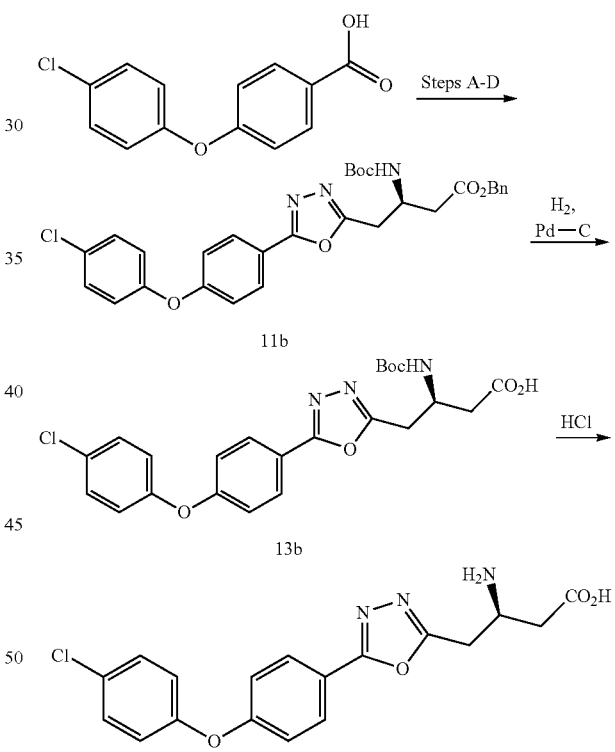

Example 25

Steps A-D: (R)-benzyl 3-((tert-butoxycarbonyl) amino)-4-(5-(4-(4-chlorophenoxy) phenyl)-1,3,4-oxadiazol-2-yl)butanoate (11b)

This compound was synthesised in four steps analogously to compound 11a starting from commercially available 4-(4-chlorophenoxy)benzoic acid.

M/z=564.2 [M+H]+, Rt=1.39 min (UPLC-MS conditions a), $^1$H NMR (400 MHz, DMSO-$d_6$) δ=7.96 (d, 2H), 7.51 (d, 2H), 7.30-7.40 (m, 5H), 7.15-7.20 (m, 4H), 5.09 (s, 2H), 4.28 (br m, 1H), 3.16 (dd, 1H), 3.02 (dd, 1H), 2.7 (dd, 1H), 2.70 (dd, 1H), 1.28 (s, 9H) ppm.

Step E: (R)-3-((tert-butoxycarbonyl)amino)-4-(5-(4-(4-chlorophenoxy)phenyl)-1,3,4-oxadiazol-2-yl)butanoic acid (13b)

(R)-benzyl 3-((tert-butoxycarbonyl) amino)-4-(5-(4-(4-chlorophenoxy) phenyl)-1,3,4-oxadiazol-2-yl)butanoate (11b, 420 mg, 0.745 mmol) was dissolved in methanol (8 mL) and added to a flask containing 10% Pd/C (79.0 mg, 0.074 mmol) under argon. The mixture was degassed and flushed with hydrogen three times. The reaction mixture was stirred under an atmosphere of hydrogen for 3 h at rt. The reaction mixture was filtered over a pad of celite and evaporated under reduced pressure. The product 13b was used in the next step without further purification.

M/z=474.1 [M+H]$^+$, Rt=1.13 min (UPLC-MS conditions a), $^1$H NMR (400 MHz, DMSO-d$_6$) δ=12.29 (s, br, 1H), 7.98 (d, 2H), 7.51 (d, 2H), 7.13-7.22 (m, 4H), 4.21 (m, 1H), 3.14 (m, 1H), 3.01 (m, 1H), 2.54-2.57 (m, 2H), 1.28 (s, 9H) ppm.

Step F: (R)-3-amino-4-(5-(4-(4-chlorophenoxy)phenyl)-1,3,4-oxadiazol-2-yl)butanoic acid (Example 25)

This compound was synthesized in analogy to 12a from 13b. The product was purified by flash column chromatography on silica (methanol:EtOAc from 0:1 to 2:1) and example 25 was so obtained as the zwitterionic salt.

M/z=374.1 [M+H]$^+$, Rt=0.78 min (UPLC-MS conditions a), $^1$H NMR (400 MHz, DMSO-d$_6$) δ=8.01 (d, 2H), 7.51 (d, 2H), 7.17-7.22 (m, 4H), 3.80 (m, 1H), 3.65 (m, 1H), 2.89 (m, 1H), 2.79 (d, 2H) ppm.

Example 26

(R)-3-amino-4-(3-(4-(4-chlorophenoxy)phenyl)-1,2,4-oxadiazol-5-yl)butanoic acid

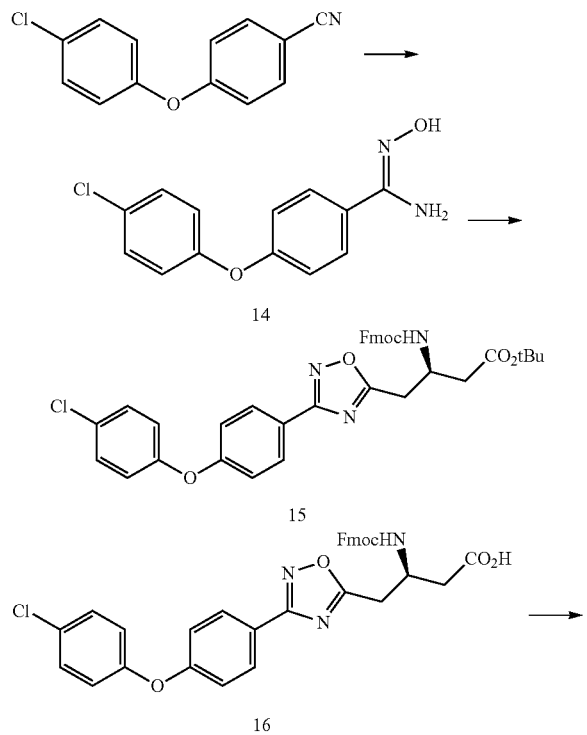

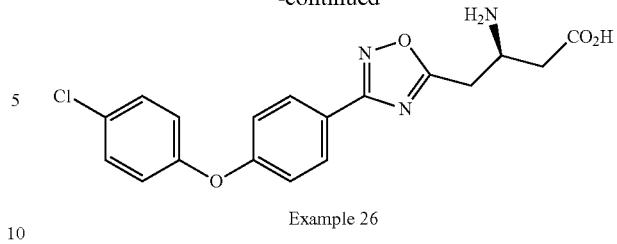

Example 26

Step A: 4-(4-chlorophenoxy)-N'-hydroxybenzimidamide (14)

A solution of 4-(4-chlorophenoxy)benzonitrile (1.00 g, 4.35 mmol) in EtOH (15 mL) was treated with hydroxylamine (50% in water, 1.03 mL. 17.4 mmol) and heated to reflux for 1 h. The reaction mixture was concentrated i. vac. and the residue was recrystallized from refluxing EtOH to afford the desired product 14 as a colorless solid.

M/z=263.3 [M+H]$^+$, Rt=0.82 min (UPLC-MS conditions a), $^1$H NMR (400 MHz, DMSO-d$_6$) δ=9.60 (s, 1H), 7.70 (d, 2H), 7.45 (d, 2H), 7.07 (d, 2H), 7.02 (d, 2H), 5.80 (s, 2H) ppm.

Step B: (R)-tert-butyl 3-((((9H-fluoren-9-yl)methoxy)carbonyl)amino)-4-(3-(4-(4-chlorophenoxy)phenyl)-1,2,4-oxadiazol-5-yl)butanoate (15)

A suspension of Fmoc-beta-Glu(OtBu)—OH (250 mg, 0.588 mmol), HATU (246 mg, 0.646 mmol) and DIPEA (0.205 mL, 1.18 mmol) in 2-MeTHF (5 mL) was stirred at rt for 1 h. 4-(4-chlorophenoxy)-N'-hydroxybenzimidamide (14, 170 mg, 0.646 mmol) was added, and the vial was capped and heated to 90° C. for 17 h. All volatiles were removed i. vac. and the residue was purified by flash column chromatography on RP18 silica (0.1% TFA in water:MeCN from 9:1 to 0:1) to afford oxadiazole 15 as a pale yellow viscous oil.

M/z=652.1 [M+H]$^+$, Rt=1.56 min (UPLC-MS conditions a).

Step C: (R)-3-((((9H-fluoren-9-yl)methoxy)carbonyl)amino)-4-(3-(4-(4-chlorophenoxy)phenyl)-1,2,4-oxadiazol-5-yl)butanoic acid (16)

A solution of (R)-tert-butyl 3-((((9H-fluoren-9-yl)methoxy)carbonyl)amino)-4-(3-(4-(4-chlorophenoxy)phenyl)-1,2,4-oxadiazol-5-yl)butanoate (15, 233 mg, 0.339 mmol) in DCM (6 mL) was treated with TFA (4 mL) and kept at rt for 1 h. All volatiles were removed i. vac. and the residue was purified by flash column chromatography on RP18 silica (0.1% TFA in water:MeCN from 9:1 to 0:1) to afford acid 16 as a yellow foam.

M/z=596.1 [M+H]$^+$, Rt=1.36 min (UPLC-MS conditions a).

Step D: (R)-3-amino-4-(3-(4-(4-chlorophenoxy)phenyl)-1,2,4-oxadiazol-5-yl)butanoic acid Example 26

A solution of (R)-3-((((9H-fluoren-9-yl)methoxy)carbonyl)amino)-4-(3-(4-(4-chlorophenoxy)phenyl)-1,2,4-oxadiazol-5-yl)butanoic acid (16, 205 mg, 0.344 mmol) in DCM (10 mL) was treated with piperidine (0.511 mL, 5.16 mmol) and stirred at rt for 3 h. All volatiles were removed i. vac. and the residue was purified by flash column chromatography on RP18 silica (890 mg/L ammonium carbonate in water:MeCN from 9:1 to 0:1) to afford the desired product (Example 26) as a colorless zwitterion.

M/z=374.0 [M+H]+, Rt=3.14 min (UPLC-MS conditions b), ¹H NMR (400 MHz, DMSO-d$_6$) δ=8.03 (d, 2H), 7.50 (d, 2H), 7.18 (d, 2H), 7.16 (d, 2H), 3.50-3.61 (m, 1H), 3.18 (dd, 1H), 3.11 (dd, 1H), 2.41 (dd, 1H), 2.26 (dd, 1H) ppm.

Example 27

(R)-3-amino-4-(3-(4-(4-chlorophenoxy)phenyl)-1,2,4-oxadiazol-5-yl)butanamide

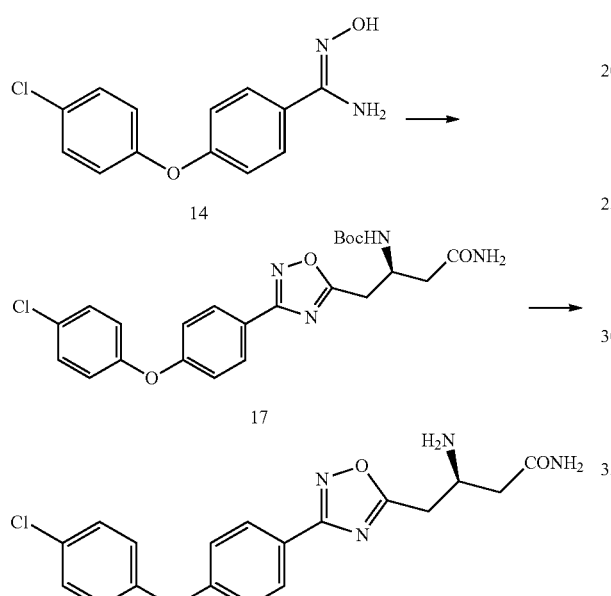

Example 27

Step A: (R)-tert-butyl (4-amino-1-(3-(4-(4-chlorophenoxy)phenyl)-1,2,4-oxadiazol-5-yl)-4-oxobutan-2-yl)carbamate (17)

This compound was synthesized in analogy to 15 from 14 and commercially available Boc-beta-Gln-OH.

M/z=473.0 [M+H]+, Rt=1.17 min (UPLC-MS conditions a).

Step B: (R)-3-amino-4-(3-(4-(4-chlorophenoxy)phenyl)-1,2,4-oxadiazol-5-yl)butanamide Example 27

A solution of (R)-tert-butyl (4-amino-1-(3-(4-(4-chlorophenoxy)phenyl)-1,2,4-oxadiazol-5-yl)-4-oxobutan-2-yl)carbamate (17, 91.8 mg, 0.194 mmol) in DCM (6 mL) and TFA (4 mL) was stirred for 1 h at rt. All volatiles were removed i. vac. and the residue was purified by flash column chromatography on RP18 silica (0.1% TFA in water:MeCN from 9:1 to 0:1). The product containing fractions were treated with 0.1 N HCl (4 mL) and concentrated i. vac. The residue was triturated with acetone (2 mL) and heptane (2 mL) and collected by filtration affording the hydrochloride of Example 27 as a colorless powder.

M/z=373.1 [M+H]+, Rt=2.68 min (UPLC-MS conditions b), ¹H NMR (400 MHz, DMSO-d$_6$) δ=8.22 (s, br, 3H), 8.05 (d, 2H), 7.69 (s, br, 1H), 7.51 (d, 2H), 7.22 (s, br, 1H), 7.15-7.21 (m, 4H), 3.92-4.01 (m, 1H), 3.40 (d, 2H), 2.60-2.67 (m, 2H) ppm.

Example 28

(S)-3-amino-4-(4-(4-(4-chlorophenoxy)phenyl)-1H-pyrazol-1-yl)butanoic acid

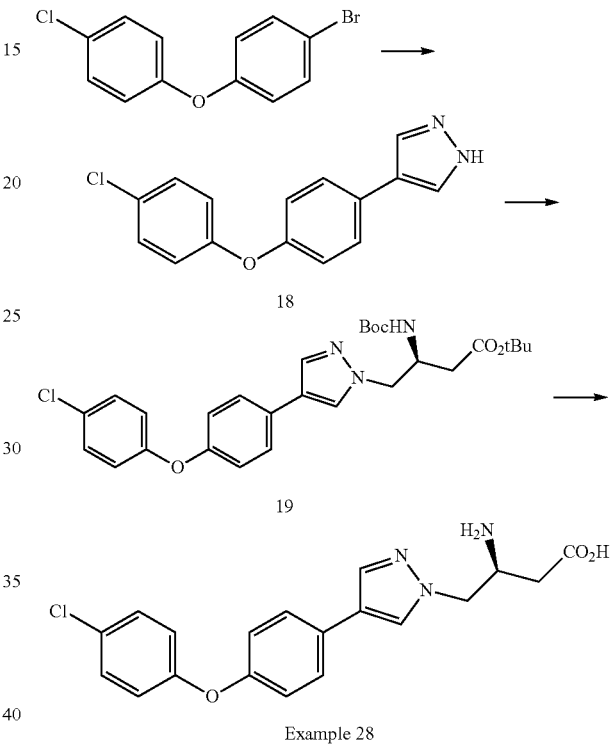

Example 28

Step B: 4-(4-(4-chlorophenoxy)phenyl)-1H-pyrazole (18)

A suspension of 1-bromo-4-(4-chlorophenoxy)benzene (170 mg, 0.600 mmol), 4-pyrazoleboronic acid pinacol ester (140 mg, 0.719 mmol), Pd(PPh$_3$)$_2$Cl$_2$ (42.1 mg, 0.060 mmol) and aqueous K$_2$CO$_3$ (2 N, 0.749 mL, 1.50 mmol) in n-propanol (5 mL) was heated in a microwave to 100° C. for 90 min. The reaction mixture was diluted with EtOAc (30 mL) and washed with sat. Na$_2$CO$_3$ (15 mL), water (15 mL) and brine (20 mL). The organic phase was dried over Na$_2$SO$_4$, filtered and concentrated i. vac. Purification by flash column chromatography on RP18 silica (0.1% TFA in water:MeCN from 9:1 to 4:6) afforded pyrazole 18 as a colorless solid.

M/z=271.1 [M+H]+, Rt=1.10 min (UPLC-MS conditions a), ¹H NMR (400 MHz, MeOD-d$_4$) δ=7.94 (s, 2H), 7.60 (d, 2H), 7.35 (d, 2H), 7.03 (d, 2H), 7.00 (d, 2H) ppm.

Step C: (S)-tert-butyl 3-((tert-butoxycarbonyl)amino)-4-(4-(4-(4-chlorophenoxy)phenyl)-1H-pyrazol-1-yl)butanoate (19)

A solution of 4-(4-(4-chlorophenoxy)phenyl)-1H-pyrazole (18, 200 mg, 0.739 mmol) in 2-MeTHF (2.4 mL) was cooled to −78° C. Solid sodium hydride (60% in mineral oil, 35.5 mg, 0.813 mmol) was added, followed by 2a (305 mg, 0.813 mmol) in 2-MeTHF (1 mL). The reaction mixture was allowed to warm up to rt over a period of 1 h. The reaction mixture was partitioned between 0.1 N HCl (20 mL) and EtOAc (30 mL). The aqueous layer was extracted with EtOAc (3×30 mL) and the combined organic extracts were washed with brine, dried over $Na_2SO_4$, filtered and concentrated i. vac. The residue was purified by flash column chromatography on RP18 silica (0.1% TFA in water:MeCN from 9:1 to 0:1) to afford the title compound 19 as a yellow solid in sufficient purity (ca. 70%) for the next step.

M/z=+529.2 [M+H]$^+$, Rt=1.45 min (UPLC-MS conditions a).

Step D: (S)-3-amino-4-(4-(4-(4-chlorophenoxy)phenyl)-1H-pyrazol-1-yl)butanoic acid Example 28

Intermediate 19 was deprotected in analogy to Method G. Purification by flash column chromatography on RP18 silica (0.1% TFA in water:MeCN from 9:1 to 0:1) afforded the desired compound which was suspended in a minimal amount of acetone and treated with HCl in $Et_2O$ (2 N, 1 mL, 2 mmol). The hydrochloride of Example 28 was collected by filtration and obtained as a slightly yellowish powder.

M/z=372.2 [M+H]$^+$, Rt=3.08 min (UPLC-MS conditions b), $^1$H NMR (400 MHz, MeOD-d$_4$) δ=8.02 (s, 1H), 7.94 (s, 1H), 7.60 (d, 2H), 7.36 (d, 2H), 7.04 (d, 2H), 7.00 (d, 2H), 4.45-4.60 (m, 2H), 4.04-4.11 (m, 1H), 2.77 (dd, 1H), 2.65 (dd, 1H) ppm.

Example 29

(S)-3-amino-4-(5-(4-((5-chloro-3-fluoropyridin-2-yl)oxy)phenyl)-2H-tetrazol-2-yl)butanoic acid

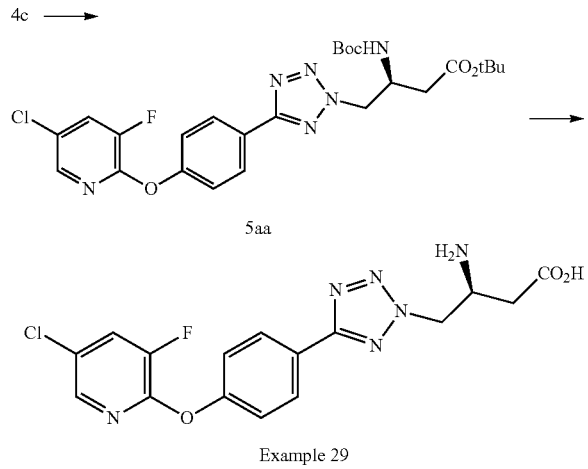

Step A: (S)-tert-butyl 3-((tert-butoxycarbonyl)amino)-4-(5-(4-((5-chloro-3-fluoropyridin-2-yl)oxy)phenyl)-2H-tetrazol-2-yl)butanoate (5aa)

Intermediate 5aa was prepared from tetrazole 4c in analogy to Method C, and obtained as a colorless foam.

M/z=549.3 [M+H]$^+$, Rt=6.26 min (UPLC-MS conditions b), $^1$H NMR (400 MHz, DMSO-d$_6$) δ=8.28 (dd, 1H), 8.10-8.14 (m, 2H), 8.09 (s, br, 1H), 7.41 (d, 2H), 7.01 (d, 1H), 4.85 (dd, 1H), 4.65 (dd, 1H), 4.27-4.36 (m, 1H), 2.63 (dd, 1H), 2.45 (dd, 1H), 1.40 (s, 9H), 1.25 (s, 9H) ppm, $^{19}$F NMR (376 MHz, DMSO-d$_6$) δ=−134.0 (d, 1F) ppm.

Step B: (S)-3-amino-4-(5-(4-((5-chloro-3-fluoropyridin-2-yl)oxy)phenyl)-2H-tetrazol-2-yl)butanoic acid (Example 29)

Deprotection of intermediate 5aa in analogy to Method G afforded the hydrochloride of Example 29 as a colorless powder.

M/z=393.1 [M+H]$^+$, Rt=2.47 min (UPLC-MS conditions b), Rt=14.85 min (HPLC conditions h), $^1$H NMR (400 MHz, MeOD-d$_4$) δ=8.24 (d, 2H), 7.98 (d, 1H), 7.91 (dd, 1H), 7.36 (d, 2H), 5.17 (d, 2H), 4.25-4.34 (m, 1H), 2.96 (dd, 1H), 2.80 (dd, 1H) ppm, $^{19}$F NMR (376 MHz, MeOD-d$_4$) δ=−135.7 (d, 1F) ppm.

Biological Part

A compound of formula (I) or a pharmaceutically acceptable salt thereof, exhibit valuable pharmacological properties, e.g. properties susceptible to LTA4H, e.g. as indicated in tests as provided in the next sections and are therefore indicated for therapy related to LTA4H.

a) Human LTA4H Enzyme Assay:

Leukotriene A4 hydrolase (LTA4H) catalyzes the vinylogous hydrolysis of the epoxide, leukotriene A4 (LTA4) into the pro-inflammatory mediator LTB4. LTA4H is also able to catalyze the hydrolysis of di- and tripeptide substrates, as well as the chromogenic 7-amino-4-methylcoumarin (AMC) derivatives of amino acids. The AMC derivative of Arginine (Arg-AMC) can be used as a surrogate substrate for LTA4H and enables the measurement of enzyme activity and compound IC$_{50}$ values by monitoring the fluorescence intensity upon AMC release.

For compound testing, compounds are delivered as 10 mM stock solutions in 90% DMSO (10% water) in matrix tubes. From this, a 1:5 dilution series is prepared with a starting concentration of 10 mM going down to 0.64 µM. For the enzymatic assay 0.5 µL of compound solution is transferred to each well and 24.5 µL of assay buffer (50 mM Tris buffer, pH 7.5, 150 mM NaCl, 10 mM CaCl$_2$) is added to the well followed by 25 µL of enzyme solution (36 nM human LTA4H in assay buffer). The enzyme compound mixture is incubated at room temperature for 15 minutes prior to the addition of 50 µL substrate solution. A final substrate concentration of 600 µM, which is around the K$_M$ value of Arg-AMC, at a final enzyme concentration of 9 nM is chosen. Upon addition of the substrate, the plate is immediately placed in a fluorescence reader and the fluorescence is measured every 10 minutes for 60 minutes using the filter setting λ$_{excitation}$=380 nm and λ$_{emission}$=460 nm. AMC at varying concentrations (0.00128-100 µM) in assay buffer is used as a standard curve. Raw data is converted to rate (moles per minute) using the AMC calibration curve calculated from the AMC standards. The data is analyzed in GraphPad Prism (GraphPad software Inc.) using non-linear regression to determine IC$_{50}$ values of LTA4H inhibitors.

Due to the assay setup, the maximally detectable potency of compounds is at around 2-3 nM. Therefore compounds with a potency that may theoretically result in IC$_{50}$ values lower than 2 nM are given as 2 nM (=lower cutoff of assay). The potencies of the tested compounds are shown in table 1 (mean values of at least 3 measurements were provided).

b) Human Whole Blood Assay:

Compounds are tested in a human whole blood assay (hWB) to test their ability to inhibit LTB4 biosynthesis in a human cellular system. To this end, fresh blood is collected in heparinized vacutainers by venipuncture from volunteers. Blood is diluted 1:3 with RPMI (Roswell Park Memorial Institute) medium and aliquots of 200 µL are transferred to 96-well round bottom cell culture plates. For compound testing, compounds are delivered as 10 mM stock solutions in 90% DMSO in matrix tubes. From this, a four-fold serial dilution is prepared with a starting concentration of 250 µM going down to 2.45 µM. 4 µL of compound dilution or vehicle is added to 200 µL of blood and incubated for 15 min at 37° C. in a humidified incubator. Then blood is stimulated with 10 µg/ml calcium ionophore A23187 (Sigma) or equal volume DMSO (control) and incubated for an additional 15 min at 37° C. in a humidified incubator. Incubation is terminated by centrifugation at 300 g for 10 min at 22° C. Plasma supernatant is taken and transferred to a 96 well plate for eicosanoid determination by ELISA (Assay designs) according to the manufacturer's protocol after 1:20 dilution in assay buffer. The data is analyzed in GraphPad Prism (GraphPad software Inc.) using non-linear regression to determine $IC_{50}$ values of LTA4H inhibitors. The potencies of the tested compounds are shown in table 1.

TABLE 1

| Example No. | ArgAMC $IC_{50}$ (nM) | hWB $IC_{50}$ (nM) |
|---|---|---|
| 1 | 2 | 227 |
| 2 | 3 | 252 |
| 3 | 3 | 166 |
| 4 | 3 | 141 |
| 5 | 3 | 396 |
| 6 | 2 | 63 |
| 7 | 3 | 122 |
| 8 | 3 | 282 |
| 9 | 2 | 402 |
| 10 | 4 | 214 |
| 11 | 2 | 156 |
| 12 | 3 | 119 |
| 13 | 2 | 86 |
| 14 | 3 | 78 |
| 15 | 2 | 81 |
| 16 | 3 | 165 |
| 17 | 4 | 183 |
| 18 | 4 | 156 |
| 19 | 3 | 273 |
| 20 | 5 | 270 |
| 21 | 5 | 209 |
| 22 | 8 | 294 |
| 23 | 2 | 173 |
| 24 | 3 | 282 |
| 25 | 3 | 382 |
| 26 | 3 | 126 |
| 27 | 10 | 218 |
| 28 | 3 | 728 |
| 29 | 2 | 167 | c) Murine PD Assay:

LTA4H inhibitor compounds or vehicle control (30% PEG200 (70%), 5% Glucose) is applied per os (p.o.) in a dose of 0.3 mg/kg to female C57BL/6 mice (Charles River France). Three hours after application of compound, mice are terminally bled and blood is collected in heparinized tubes. Collected blood is diluted 1:3 in RPMI medium, added in 96-well round bottom cell culture plates and incubated with 10 µg/ml calcium ionophore A23187 (Sigma) or equal volume DMSO (control) for 15 min at 37° C. in a humidified incubator. Incubation is terminated by centrifugation at 300 g for 10 min at 22° C. Plasma supernatant is taken, diluted 1:10 in assay buffer and transferred to a 96 well plate for eicosanoid determination by ELISA (Assay designs) according to the manufacturer's protocol. Percent inhibition of LTB4 release in comparison to vehicle control was calculated and is shown for the tested compounds in table 2. (For the sake of clarity: The bigger the numeric value in table 2, the stronger is the inhibition)

TABLE 2

| Example No. | PD effect [%] inhibition of LTB4 release |
|---|---|
| 1 | −58 |
| 3 | −60 |
| 4 | −56 |
| 6 | −78 |
| 7 | −57 |
| 11 | −70 |
| 12 | −81 |
| 13 | −55 |
| 14 | −71 |
| 15 | −49 |
| 16 | −9 |
| 17 | −47 |
| 23 | −44 |
| 29 | −43 |

Utilities

The compounds of the invention are especially inhibitors of LTA4H-activity and are therefore useful in treating diseases and disorders which are typically ameliorated by the inhibition of LTA4H. Such diseases and conditions may include inflammatory and autoimmune disorders and pulmonary and respiratory tract inflammation.

Accordingly, the compounds may be useful in the treatment of the following diseases or disorders: acute or chronic inflammation, anaphylactic reactions, allergic reactions, atopic dermatitis, psoriasis, acute respiratory distress syndrome, immune complex-mediated pulmonary injury and chronic obstructive pulmonary disease, inflammatory bowel diseases (including ulcerative colitis, Crohn's disease and post-surgical trauma), gastrointestinal ulcers, neutrophilic dermatoses (including but not limited to Pyoderma gangrenosum, Sweet's syndrome, severe acne and neutrophilic urticaria), immune-complex-mediated glomerulonephritis, autoimmune diseases (including insulin-dependent diabetes mellitus, multiple sclerosis, rheumatoid arthritis, osteoarthritis and systemic lupus erythematosus), vasculitides (including but not limited to cutaneous vasculitis, Behcets disease and Henoch Schönlein Purpura), cardiovascular disorders (including, but not limited to hypertension, atherosclerosis, aneurysm, critical leg ischemia, peripheral arterial occlusive disease, pulmonary artery hypertension and Reynaud's syndrome), sepsis, inflammatory and neuropathic pain including arthritic pain, periodontal disease including gingivitis, ear infections, migraine, benign prostatic hyperplasia, Sjogren-Larsson Syndrome and cancers (including, but not limited to, leukemias and lymphomas, prostate cancer, breast cancer, lung cancer, malignant melanoma, renal carcinoma, head and neck tumors and colorectal cancer).

Compounds of the invention are especially useful in the treatment of acute or chronic inflammation especially autoinflammatory disorders such as sterile neutrophilic inflammatory disorders, inflammatory bowel disease (including ulcerative colitis and Crohn's disease), neutrophilic dermatoses (including Pyoderma gangrenosum and severe acne), vasculitides, rheumatoid arthritis, gout and cardiovascular diseases.

Combinations

The compound of the present invention may be administered either simultaneously with, or before or after, one or more other therapeutic agent. The compound of the present invention may be administered separately, by the same or different route of administration, or together in the same pharmaceutical composition as the other agents.

The compounds of the invention may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent.

For example, the compounds of the invention may be used in combination with a COX inhibitor, a Cysteinyl-Leukotriene Receptor antagonist (including Montelukast, Pranlukast, Zafirlukast), a leukotriene C4 synthase (LTC4S) inhibitor, a statin, sulfasalazine, Mesalamine, a calcineurin inhibitor, e.g. cyclosporin A or FK 506; a mTOR inhibitor, e.g. rapamycin, 40-O-(2-hydroxyethyl)-rapamycin, biolimus-7 or biolimus-9; an ascomycin having immunosuppressive properties, e.g. ABT-281, ASM981; corticosteroids; cyclophosphamide; azathioprene; methotrexate; leflunomide; mizoribine; mycophenolic acid or salt; mycophenolate mofetil; IL-1beta inhibitor.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a co-agent, are both administered to a patient simultaneously in the form of a single entity or dosage.

The term "non-fixed combination" means that the active ingredients, e.g. a compound of formula (I) and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by LTA4H. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

The invention claimed is:
1. A method of preparing (S)-3-amino-4-(5-(4-((5-chloro-3-fluoropyridin-2-yl)oxy)phenyl)-2H-tetrazol-2-yl)butanoic acid or a pharmaceutically acceptable salt thereof:

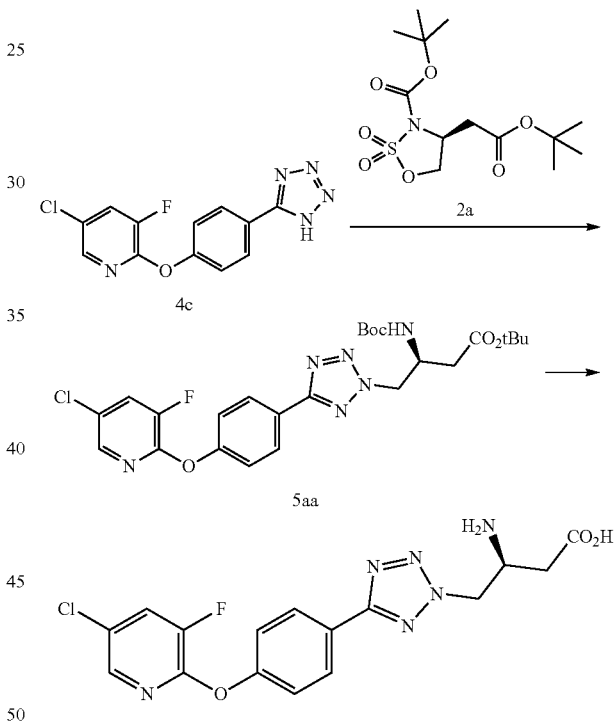

said method comprising the steps of
a) reacting a compound of Formula (4c) with a compound of Formula (2a) to form a compound of Formula (5aa) and
b) converting the compound of Formula (5aa) to S)-3-amino-4-(5-(4-((5-chloro-3-fluoropyridin-2-yl)oxy)phenyl)-2H-tetrazol-2-yl)butanoic acid.

* * * * *